(12) United States Patent
Matsumoto et al.

(10) Patent No.: US 8,920,726 B2
(45) Date of Patent: Dec. 30, 2014

(54) BLOOD ANALYZER, BLOOD ANALYSIS METHOD, HEMOLYTIC AGENT AND STAINING AGENT

(75) Inventors: Hideaki Matsumoto, Takasago (JP); Kinya Uchihashi, Kakogawa (JP); Yuji Itose, Kako-gun (JP); Aya Konishi, Nishinomiya (JP); Ayumu Yoshida, Kobe (JP)

(73) Assignee: Sysmex Corporation, Hyogo (JP)

( * ) Notice: Subject to any disclaimer, the term of this patent is extended or adjusted under 35 U.S.C. 154(b) by 938 days.

(21) Appl. No.: 12/942,752

(22) Filed: Nov. 9, 2010

(65) Prior Publication Data

US 2011/0053212 A1    Mar. 3, 2011

Related U.S. Application Data

(63) Continuation of application No. PCT/JP2009/058327, filed on Apr. 28, 2009.

(30) Foreign Application Priority Data

May 9, 2008   (JP) .................... 2008-123403

(51) Int. Cl.
| | | |
|---|---|---|
| *G01N 33/00* | (2006.01) | |
| *G01N 1/00* | (2006.01) | |
| *G01N 33/569* | (2006.01) | |
| *G01N 33/50* | (2006.01) | |
| *B01L 3/00* | (2006.01) | |

(52) U.S. Cl.
CPC ...... *G01N 33/56905* (2013.01); *G01N 33/5094* (2013.01); *G01N 2333/44* (2013.01)
USPC .............................. 422/73; 422/502; 73/61.59

(58) Field of Classification Search
USPC ............................................ 422/73; 73/61.59
See application file for complete search history.

(56) References Cited

U.S. PATENT DOCUMENTS

| | | | |
|---|---|---|---|
| 6,210,969 B1 | 4/2001 | Li et al. | |
| 2005/0221396 A1 | 10/2005 | Simon-Lopez | |
| 2006/0210438 A1 | 9/2006 | Nagai et al. | |
| 2006/0223137 A1 | 10/2006 | Yoshida et al. | |
| 2006/0250604 A1* | 11/2006 | Hamada et al. | 356/39 |
| 2007/0020721 A1* | 1/2007 | Yoshida et al. | 435/34 |
| 2007/0109530 A1* | 5/2007 | Ueno et al. | 356/39 |
| 2007/0179715 A1 | 8/2007 | Ariyoshi | |

FOREIGN PATENT DOCUMENTS

| | | |
|---|---|---|
| EP | 1 406 088 A2 | 4/2004 |
| EP | 1 746 407 A2 | 2/2007 |
| EP | 2012120 A1 | 1/2009 |
| JP | 05-322882 A | 12/1993 |

(Continued)

*Primary Examiner* — Jill Warden
*Assistant Examiner* — Brittany Fisher
(74) *Attorney, Agent, or Firm* — Sughrue Mion, PLLC

(57) ABSTRACT

This blood analyzer includes a sample preparation portion preparing a first measurement sample containing a blood sample and a hemolytic agent and a second measurement sample containing the blood sample, the same hemolytic agent as the hemolytic agent and a staining agent and a control portion classifying white blood cells in the first measurement sample into at least four groups of monocytes, neutrophils, eosinophils and others on the basis of fluorescent information and two types of scattered light information generated by a light information generation portion and classifying blood cells in the second measurement sample into at least malaria-infected red blood cells and others on the basis of fluorescent information and scattered light information generated by the light information generation portion.

12 Claims, 15 Drawing Sheets

(56) References Cited

FOREIGN PATENT DOCUMENTS

| | | |
|---|---|---|
| JP | 10-293131 A | 11/1998 |
| JP | 2000-346839 A | 12/2000 |
| JP | 2005-333868 A | 12/2005 |
| JP | 2006-292738 A | 10/2006 |
| JP | 2006-304774 A | 11/2006 |
| JP | 2006-313151 A | 11/2006 |
| JP | 2007-024844 A | 2/2007 |
| JP | 2007-078508 A | 3/2007 |
| JP | 2007-139438 A | 6/2007 |
| JP | 2007-525674 A | 9/2007 |
| WO | 2007/129485 A1 | 11/2007 |

* cited by examiner

FIG.10

COMPOSITION OF HEMOLYTIC AGENT

| LAURYL TRIMETHYL AMMONIUM CHLORIDE | 34.1 mM |
|---|---|
| STEARYL TRIMETHYL AMMONIUM CHLORIDE | 1.7 mM |
| EDTA-2K | 1.0 g/L |
| PHOSPHATE BUFFER SOLUTION | 20 mM(pH 5.0) |
| NaCl | PROPER QUANTITY (QUANTITY TO MAKE ELECTRIC CONDUCTIVITY BE ABOUT 13 mS/cm) |
| PURIFIED WATER | 1 L |

FIG.11

STAINING FLUID (FOR MALARIA DETECTION)

[CHEMICAL FORMULA OF FLUORESCENT DYE]

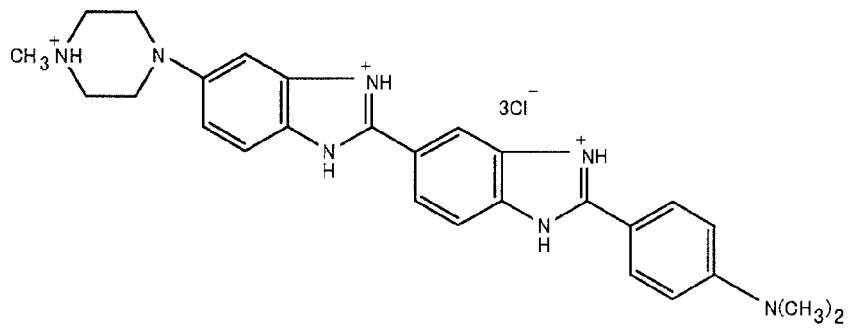

[NONIONIC SURFACTANT GROUP]

POLYOXYETHYLENE SORBITAN MONOISOSTEARATE,
POLYOXYETHYLENE SORBITAN MONOOLEATE,
POLYOXYETHYLENE HYDROGENATED CASTOR OIL,
POLYOXYETHYLENE PHYTOSTEROL,
POLYOXYETHYLENE PHYTOSTANOL,
POLYOXYETHYLENE LAURYL ETHER,
POLYOXYETHYLENE OLEYL ETHER,
POLYOXYETHYLENE POLYOXYPROPYLENE DECYL TETRADECYL ETHER,
POLYOXYETHYLENE POLYOXYPROPYLENE CETYL ETHER,
POLYOXYETHYLENE MONOLAURATE

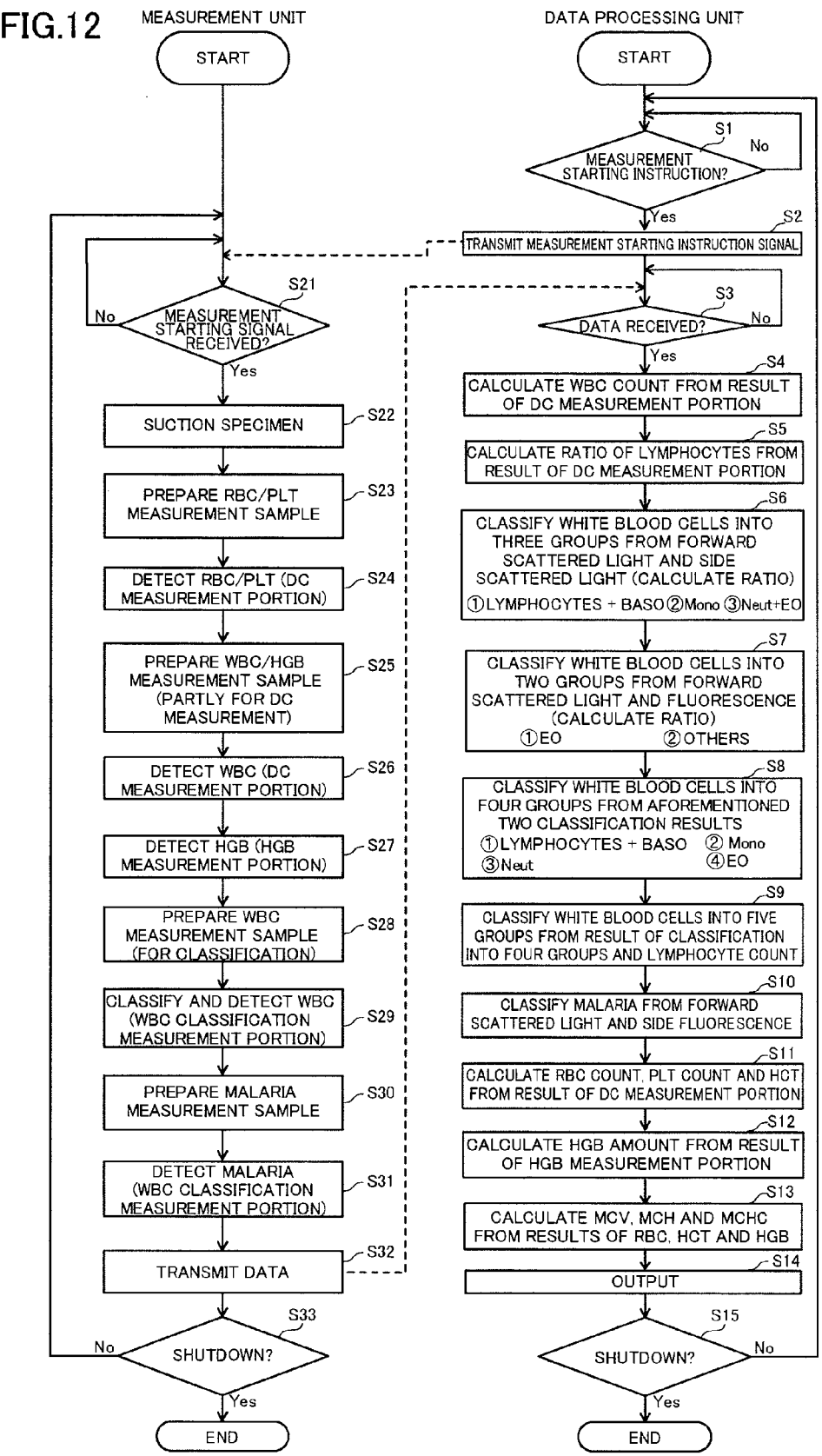

WBC PARTICLE SIZE DISTRIBUTION

BLOOD ANALYZER, BLOOD ANALYSIS METHOD, HEMOLYTIC AGENT AND STAINING AGENT

CROSS-REFERENCE TO RELATED APPLICATION

The priority application number JP2008-123403, Blood Analyzer, Blood Analysis Method, Hemolytic Agent and Staining Agent, May 9, 2008, Hideaki Matsumoto, Kinya Uchihashi, Yuji Itose, Aya Konishi and Ayumu Yoshida, upon which this patent application is based are hereby incorporated by reference. This application is a continuation of PCT/JP2009/058327, Blood Analyzer, Blood Analysis Method, Hemolytic Agent and Staining Agent, Apr. 28, 2009, Hideaki Matsumoto, Kinya Uchihashi, Yuji Itose, Aya Konishi and Ayumu Yoshida.

BACKGROUND OF THE INVENTION

1. Field of the Invention

The present invention relates to a blood analyzer, a blood analysis method, a hemolytic agent and a staining agent, and more particularly, it relates to a blood analyzer and a blood analysis method for classifying white blood cells and detecting malaria-infected red blood cells, and a hemolytic agent and a staining agent employed in this blood analysis method.

2. Description of the Background Art

A blood analyzer classifying white blood cells is known in general. Such a blood analyzer is disclosed in Japanese Patent Laying-Open No. 2006-292738, for example. Also, a blood analyzer detecting malaria-infected red blood cells is known in general. Such a blood analyzer is disclosed in Japanese Patent Laying-Open No. 2006-304774, for example.

A blood analyzer described in the aforementioned Japanese Patent Laying-Open No. 2006-292738 is configured to measure scattered light and fluorescent light and classify white blood cells in a measurement sample into four groups by a flow cytometer (light information generation portion) employing a dedicated reagent for classifying white blood cells.

A blood analyzer described in the aforementioned Japanese Patent Laying-Open No. 2006-304774 is configured to measure scattered light and fluorescent light and detect malaria-infected red blood cells in a measurement sample by a flow cytometer (light information generation portion) employing a dedicated reagent for detecting malaria-infected red blood cells.

Recently, a blood analyzer capable of both classification of white blood cells and detection of malaria-infected red blood cells has been desired.

However, the blood analyzer according to the aforementioned Japanese Patent Laying-Open No. 2006-292738 classifies white blood cells employing the dedicated reagent for classifying white blood cells, and the blood analyzer according to the aforementioned Japanese Patent Laying-Open No. 2006-304774 detects malaria-infected red blood cells employing the dedicated reagent for detecting malaria-infected red blood cells having a different composition from the reagent for classifying white blood cells, and hence two types of reagents having different compositions from each other must be developed separately to classify white blood cells and detect malaria-infected red blood cells also in a case where a blood analyzer capable of both classification of white blood cells and detection of malaria-infected red blood cells is obtained by combining the blood analyzer according to the aforementioned Japanese Patent Laying-Open No. 2006-292738 and the blood analyzer according to the aforementioned Japanese Patent Laying-Open No. 2006-304774. Consequently, there is such a problem that a user is burdened.

SUMMARY OF THE INVENTION

The present invention has been proposed in order to solve the aforementioned problems, and an object of the present invention is to provide a blood analyzer and a blood analysis method enabling classification of white blood cells in a measurement sample into four groups and detection of malaria-infected red blood cells, and a hemolytic agent and a staining agent employed in this blood analysis method.

In order to attain the aforementioned object, a blood analyzer according to a first aspect of the present invention comprises a sample preparation portion preparing a first measurement sample containing a blood sample and a hemolytic agent and a second measurement sample containing the blood sample, the same hemolytic agent as the aforementioned hemolytic agent and a staining agent, a light information generation portion generating first fluorescent information and at least two types of first scattered light information from the first measurement sample and generating second fluorescent information and second scattered light information from the second measurement sample, and a control portion performing a first classification of white blood cells in the first measurement sample into at least four groups of monocytes, neutrophils, eosinophils and others on the basis of the first fluorescent information and the two types of first scattered light information generated by the light information generation portion and classifying blood cells in the second measurement sample into at least malaria-infected red blood cells and others on the basis of the second fluorescent information and the second scattered light information generated by the light information generation portion.

In the aforementioned blood analyzer according to the first aspect, the sample preparation portion preferably further prepares a third measurement sample containing the blood sample and the hemolytic agent, and the blood analyzer preferably further comprises an electrical information generation portion generating electrical information of a sample from the third measurement sample, wherein the control portion is configured to perform a second classification of white blood cells in the third measurement sample into at least lymphocytes and others on the basis of the electrical information generated by the electrical information generation portion and classify white blood cells in the measurement samples into at least five groups of lymphocytes, basophils, monocytes, neutrophils and eosinophils on the basis of classification results of the first classification and the second classification.

In this case, the blood analyzer preferably further comprises a second light information generation portion generating at least either transmitted light information or scattered light information of a sample from the third measurement sample, wherein the control portion is configured to acquire a hemoglobin concentration in the third measurement sample on the basis of at least either the transmitted light information or the scattered light information generated by the second light information generation portion.

In the aforementioned blood analyzer according to the first aspect, a dilution magnification of the hemolytic agent in the second measurement sample is preferably different from a dilution magnification of the hemolytic agent in the first measurement sample.

In this case, the dilution magnification of the hemolytic agent in the second measurement sample is preferably smaller than the dilution magnification of the hemolytic agent in the first measurement sample.

In the aforementioned blood analyzer according to the first aspect, the sample preparation portion is preferably configured to prepare the first measurement sample by mixing the blood sample, the hemolytic agent stored in a predetermined reagent container and a predetermined quantity of diluted solution and prepare the second measurement sample by mixing the blood sample, the hemolytic agent stored in the predetermined reagent container and a quantity of the diluted solution smaller than the predetermined quantity.

In this case, the sample preparation portion is preferably configured to prepare the second measurement sample by mixing the blood sample in a state of mixing the hemolytic agent and the diluted solution.

In the aforementioned blood analyzer according to the first aspect, the sample preparation portion is preferably configured to prepare the second measurement sample by mixing at least the blood sample and the hemolytic agent stored in a second reagent container different from a first reagent container storing the hemolytic agent employed in the first measurement sample.

In this case, the hemolytic agent stored in the second reagent container is preferably diluted by at least 9 times and not more than 12 times.

In the aforementioned blood analyzer according to the first aspect, the hemolytic agent preferably includes two types of cationic surfactants.

In the aforementioned blood analyzer according to the first aspect, the staining agent may include a fluorescent dye shown in the following formula and a nonionic surfactant.

[Chemical Formula 2]

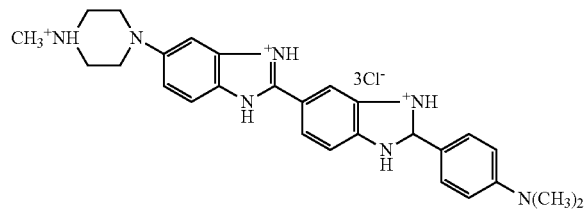

A blood analysis method according to a second aspect of the present invention comprises steps of preparing a first measurement sample containing a blood sample and a hemolytic agent and a second measurement sample containing the blood sample, the same hemolytic agent as the aforementioned hemolytic agent and a staining agent, generating first fluorescent information and at least two types of first scattered light information from the first measurement sample and generating second fluorescent information and second scattered light information from the second measurement sample, classifying white blood cells in the first measurement sample into at least four groups of monocytes, neutrophils, eosinophils and others on the basis of the first fluorescent information and the two types of first scattered light information generated from the first measurement sample, and classifying blood cells in the second measurement sample into at least malaria-infected red blood cells and others on the basis of the second fluorescent information and the second scattered light information generated from the second measurement sample.

A hemolytic agent according to a third aspect of the present invention is employed in a blood analysis method according to the second aspect of the present invention.

A staining agent according to a fourth aspect of the present invention is employed in a blood analysis method according to the second aspect of the present invention.

BRIEF DESCRIPTION OF THE DRAWINGS

FIG. 10 is a diagram showing a composition of a hemolytic agent employed in the blood analyzer according to the embodiment shown in FIG. 1.

FIG. 11 is a diagram showing a composition of a staining fluid for malaria detection employed in the blood analyzer according to the embodiment shown in FIG. 1.

FIG. 12 is a flow chart showing sample analysis processing in the blood analyzer according to the embodiment shown in FIG. 1.

DESCRIPTION OF THE PREFERRED EMBODIMENTS

An embodiment of the present invention is hereinafter described with reference to the drawings.

The structure of a blood analyzer 1 according to the embodiment of the present invention is now described with reference to FIGS. 1 to 11.

Figure 1:
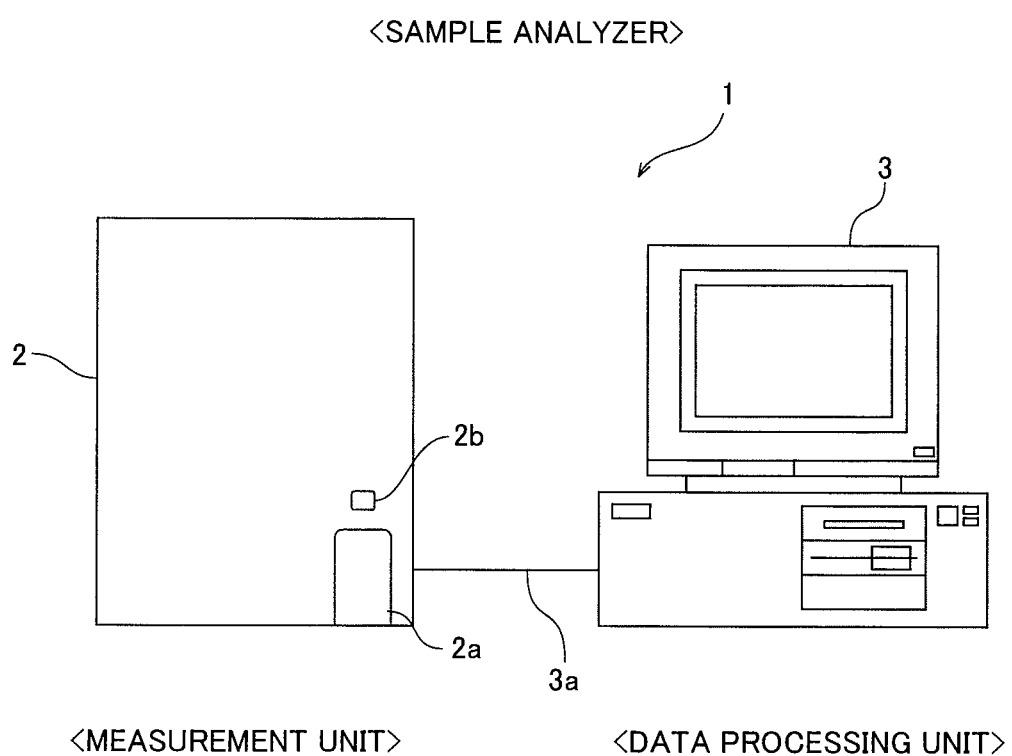
FIG. 1 is a front elevational view schematically showing the structure of a blood analyzer according to an embodiment of the present invention.

The blood analyzer 1 according to the embodiment is an apparatus employed in blood testings and mainly constituted by a measurement unit 2 and a data processing unit 3, as shown in FIG. 1. The blood analyzer 1 is set in medical facilities such as hospitals or pathology laboratories, for example. In the blood analyzer 1, the measurement unit 2 performs predetermined measurements of components contained in blood samples, and this measurement data are subjected to an analysis process when received by the data processing unit 3. The measurement unit 2 and the data processing unit 3 are so connected to each other through a data transmission cable 3a as to be capable of mutual data communication. The measurement unit 2 and the data processing unit 3 may be configured to be directly connected to each other through the data transmission cable 3a or may be connected to each other through a communication network such as a dedicated line employing a telephone line, a LAN or the Internet, for example.

Figure 2:
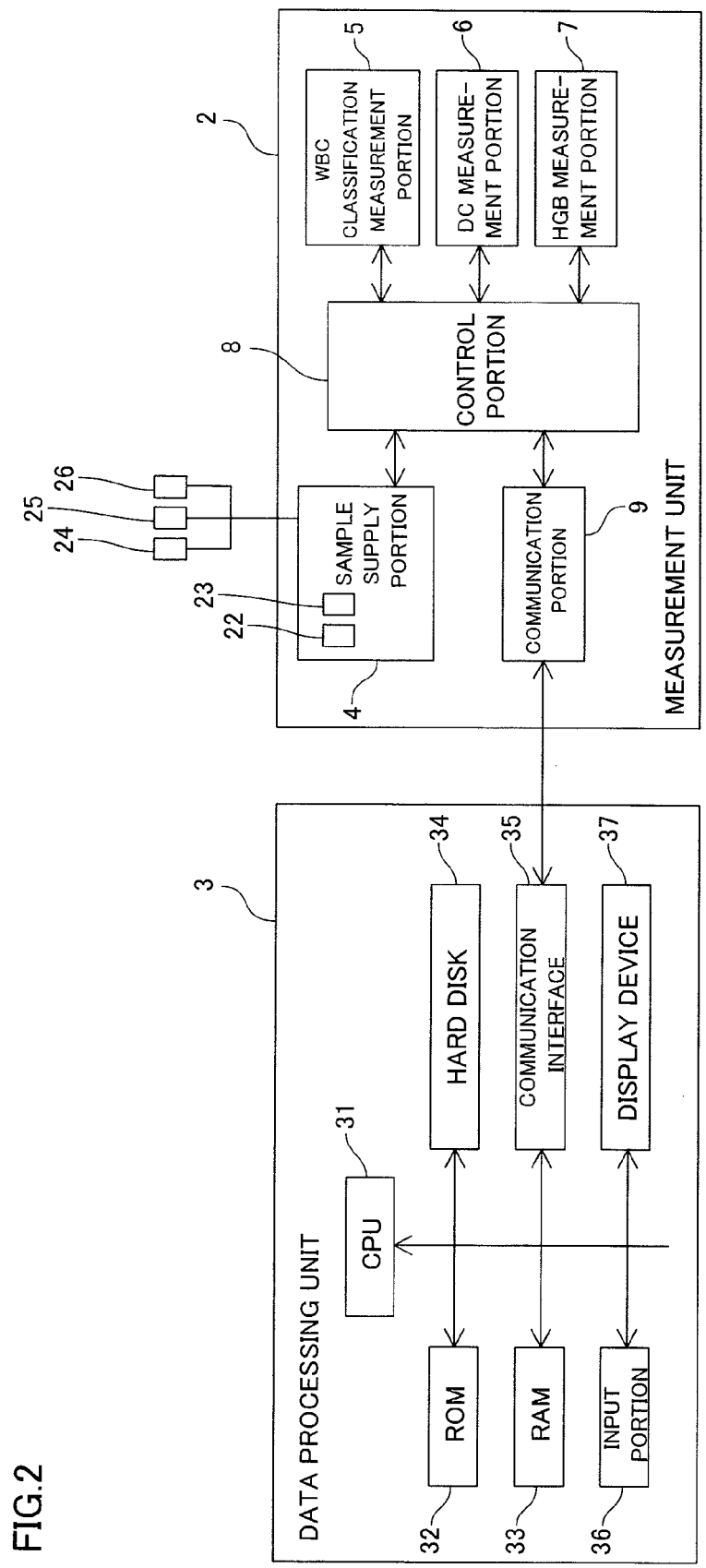
FIG. 2 is a block diagram showing the structure of the blood analyzer according to the embodiment shown in FIG. 1.
Figure 3:
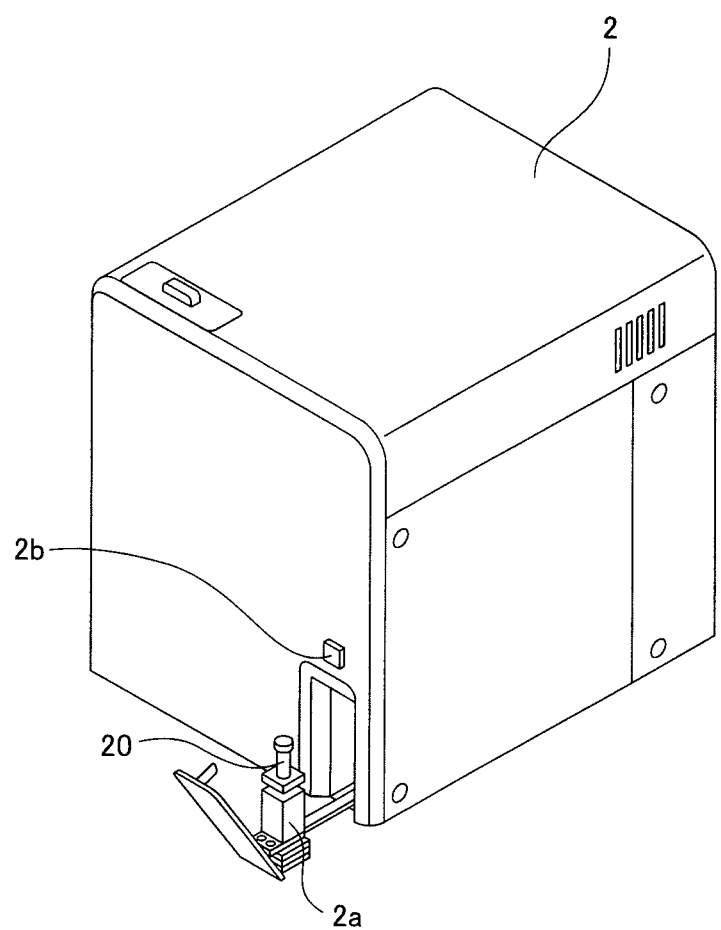
FIG. 3 is a perspective view showing a measurement unit of the blood analyzer according to the embodiment shown in FIG. 1.

The measurement unit 2 includes a sample supply portion 4, a WBC classification measurement portion 5, a DC measurement portion 6, an HGB measurement portion 7, a control portion 8 and a communication portion 9, as shown in FIG. 2. A blood collection tube set portion 2a so configured that a blood collection tube 20 storing a blood sample can be set thereon is provided at the lower right of the front of the measurement unit 2, as shown in FIG. 3. This blood collection tube set portion 2a is configured to be pushed out in a forward direction by a pressing operation of a button switch 2b provided nearby by a user. The user can set the blood collection tube 20 in a state where the blood collection tube set portion 2a is pushed out. After the blood collection tube 20 has been set, the user again presses the button switch 2b, whereby the blood collection tube set portion 2a is configured to be returned to the inside of the measurement unit 2.

Figure 4:
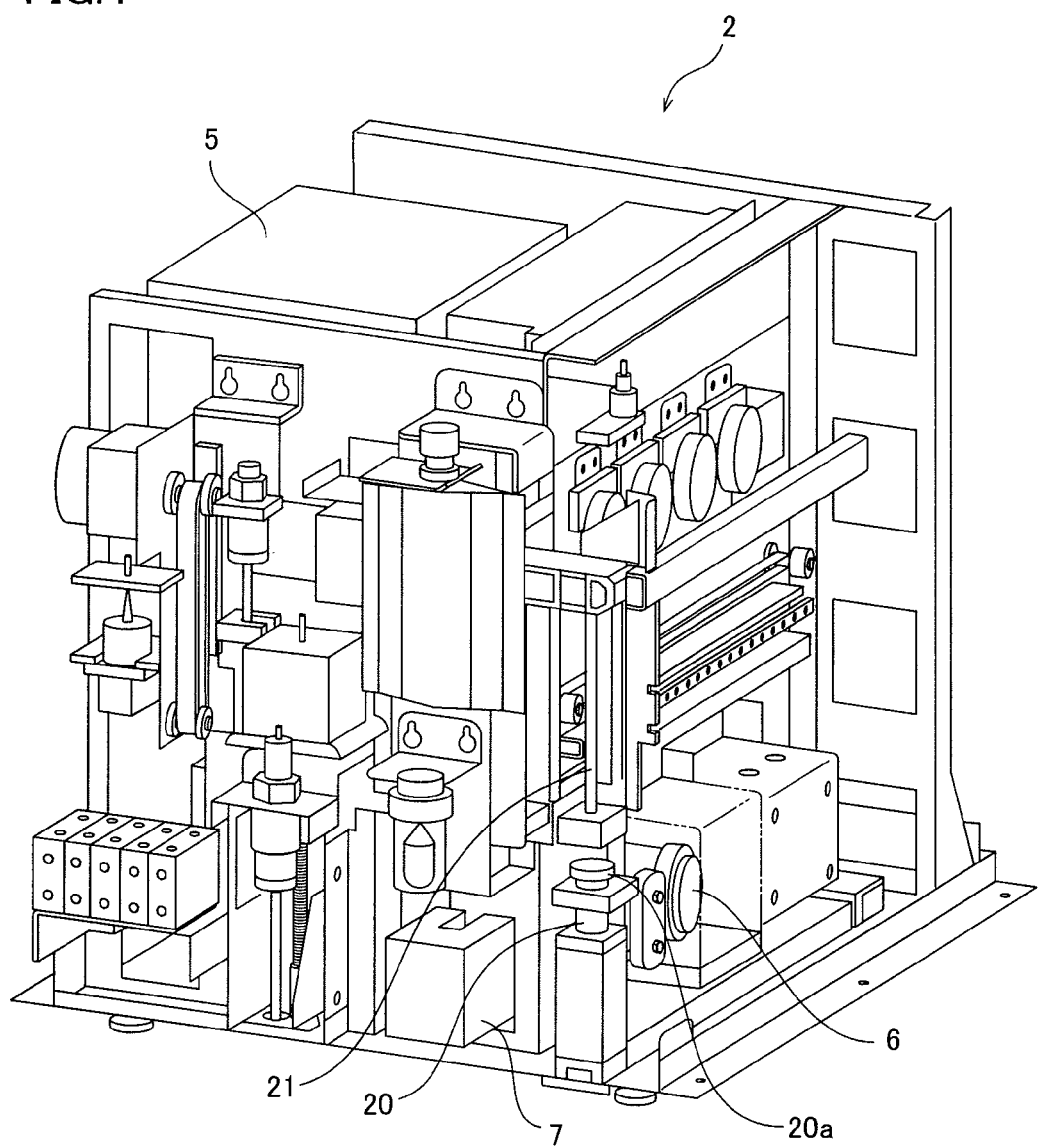
FIG. 4 is a perspective view showing the internal structure of the measurement unit of the blood analyzer according to the embodiment shown in FIG. 1.
Figure 5:
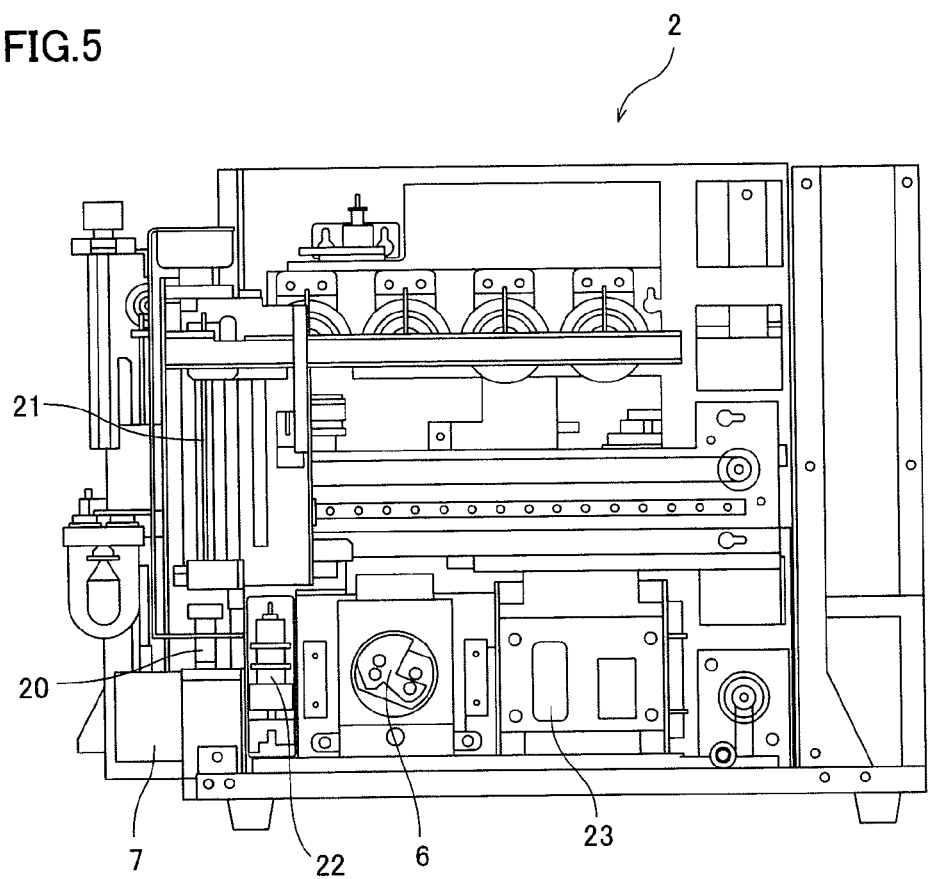
FIG. 5 is a side elevational view showing the internal structure of the measurement unit of the blood analyzer according to the embodiment shown in FIG. 1.
Figure 6:
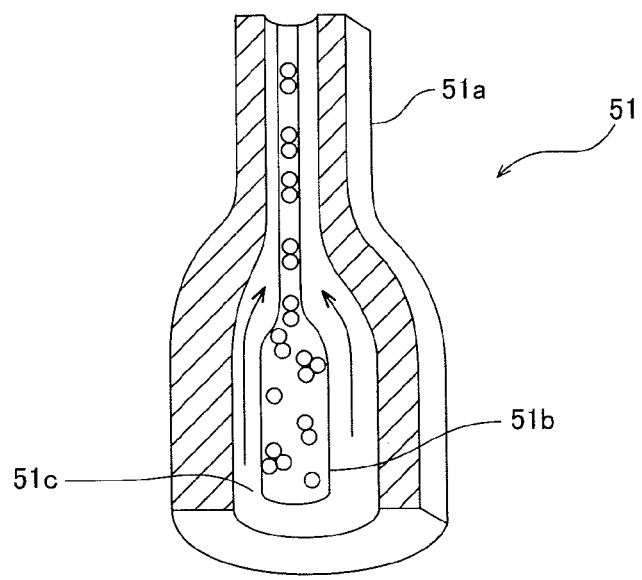
FIG. 6 is a perspective view schematically showing the structure of a flow cell provided in the measurement unit of the blood analyzer according to the embodiment shown in FIG. 1.
Figure 7:
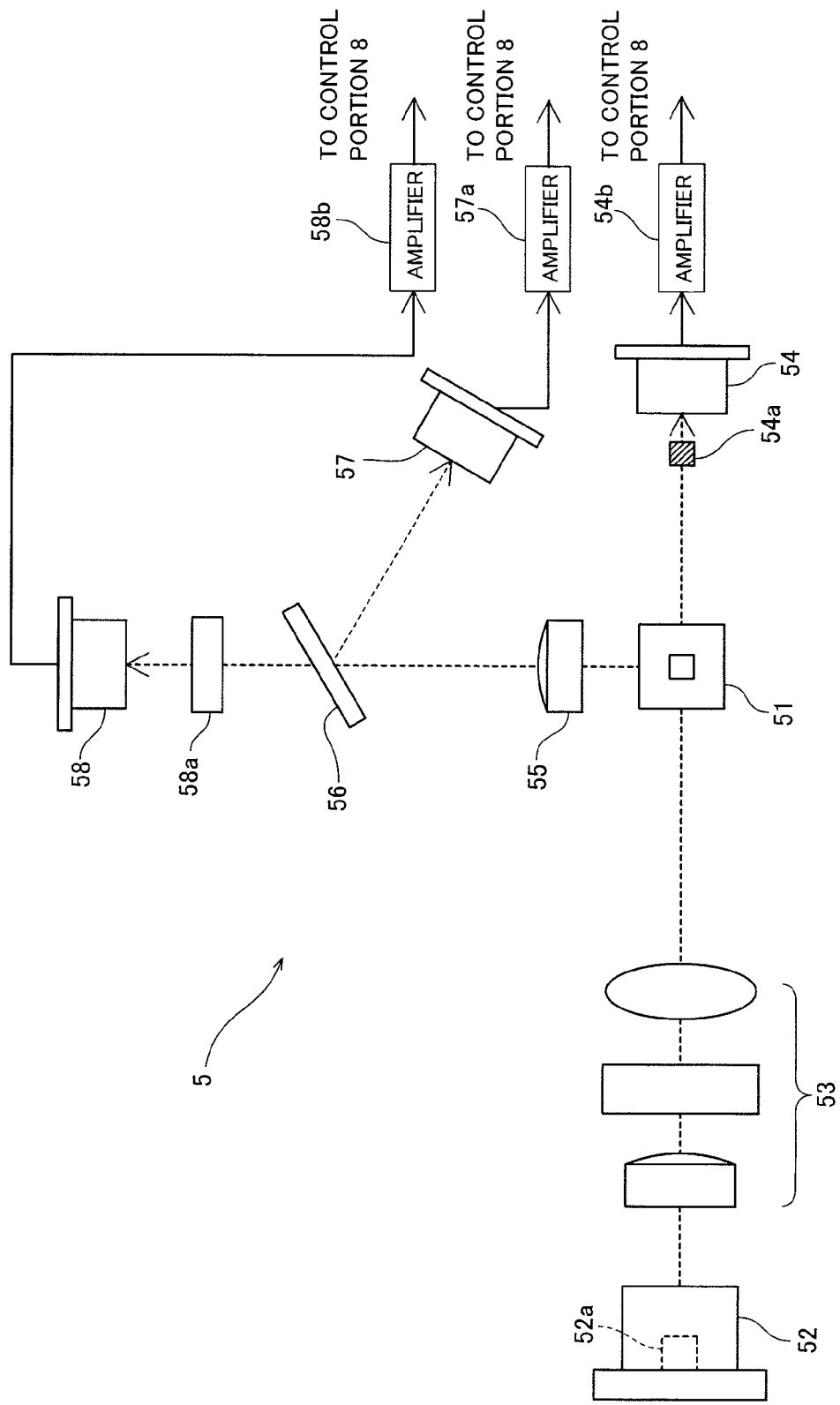
FIG. 7 is a schematic diagram showing the structure of a WBC classification measurement portion provided in the measurement unit of the blood analyzer according to the embodiment shown in FIG. 1.

A pipette 21 for suctioning measurement samples, chambers 22 and 23 (see FIG. 5) for preparation by mixing the blood sample and a reagent, and the like are provided within the measurement unit 2, as shown in FIGS. 4 and 5. The pipette 21 is formed in a shape of a tube extending vertically, and a tip thereof is sharply tapered. The pipette 21 is coupled to a syringe pump not shown in the drawings, and a predetermined quantity of liquid can be suctioned or discharged by an operation of this syringe pump. The pipette 21 is also connected to a moving mechanism and configured to be movable in vertical directions and forward and backward directions. The pipette 21 is configured to suction the blood sample stored in the blood collection tube 20 by puncturing the sharp tip into a rubber cap 20a sealing the blood collection tube 20. The pipette 21 is configured to be moved to a predetermined position by the moving mechanism and supply the blood sample to the insides of the chambers 22 and 23 after suctioning the blood sample.

The sample supply portion 4 is a flow unit having the chambers 22 and 23, a plurality of electromagnetic valves, diaphragm pumps and the like. The chamber 22 is provided for preparing a measurement sample employed in the measurement of red blood cells and platelets and the measurement of a hemoglobin concentration. The chamber 23 is provided for preparing a measurement sample employed in the measurement of white blood cells. Reagent containers are connected to the flow unit constituted by the sample supply portion 4. More specifically, a diluted solution container 24 for storing a diluted solution, a hemolytic agent container 25 for storing a hemolytic agent 100 and a staining fluid container 26 for storing a staining fluid employed in a measurement sample for detecting malaria are connected to the flow unit. Thus, the diluted solution and the hemolytic agent 100 can be supplied to the chamber 22, and the diluted solution, the hemolytic agent 100 and the staining fluid can be supplied to the chamber 23.

The WBC classification measurement portion 5 is an optical flow cytometer and provided for classifying and detecting white blood cells and detecting malaria-infected red blood cells (hereinafter referred to as detecting malaria) by a flow cytometry technique employing a semiconductor laser beam. The WBC classification measurement portion 5 has a flow cell 51 (see FIG. 6) forming a fluid flow of the measurement sample. The flow cell 51 is made of a material such as quartz having a light transmission property, glass, or synthetic resin, in a shape of a tube, and is a flow path through the interior of which a sheath fluid (diluted solution) flows. This flow cell 51 is provided with an orifice 51a, the internal cavity of which has an aperture that is narrower than the other parts. The vicinity of an inlet of the orifice 51a has a double-tube structure, and an internal side of this tube part becomes a sample nozzle 51b. A cavity on an outer side of the sample nozzle 51b is a flow path 51c through which the sheath fluid (diluted solution) flows, and the sheath fluid (diluted solution) flows through the flow path 51c and is introduced into the orifice 51a. The sheath fluid (diluted solution) supplied to the flow cell 51 in this manner flows so as to surround the measurement sample discharged from the sample nozzle 51b. Then, the measurement sample flow is constricted by the orifice 51a such that particles such as white blood cells and red blood cells contained in the measurement sample are surrounded by the sheath fluid (diluted solution) and pass through the orifice 51a one by one.

A semiconductor laser light source 52 is arranged in the WBC classification measurement portion 5 so as to emit laser beam toward the orifice 51a of the flow cell 51. This semiconductor laser light source 52 has a blue-violet semiconductor laser element 52a and is configured to be capable of emitting a blue-violet laser beam having a wavelength of about 405 nm. An illumination lens system 53 constituted by a plurality of lenses is arranged between the semiconductor laser light source 52 and the flow cell 51. Parallel beams emitted from the semiconductor laser light source 52 are collected at a beam spot by the illumination lens system 53. Furthermore, a beam stopper 54a is provided on an optical axis extending linearly from the semiconductor laser light source 52 so as to be opposed to the illumination lens system 53 and with the flow cell 51 interposed therebetween, and the beam stopper 54a is configured to block direct light from the semiconductor laser light source 52.

A photodiode 54 is arranged on an optical axis on a further downstream side of the beam stopper 54a. The photodiode 54 is configured to receive scattered light of a laser beam generated by the measurement sample flowing through the flow cell 51. More specifically, among light advancing along the optical axis extending linearly from the semiconductor laser light source 52, the direct light of the semiconductor laser light source 52 is blocked by the beam stopper 54a, and hence the photodiode 54 is configured to basically receive only scattered light (hereinafter referred to as forward scattered light) advancing along the optical axis direction. The forward scattered light emitted from the flow cell 51 is subjected to photoelectric conversion by the photodiode 54, and electrical signals (hereinafter referred to as forward scattered light signals) generated by this conversion are transmitted to an amplifier 54b. The amplifier 54b is configured to amplify the transmitted forward scattered light signals and output the amplified forward scattered light signals to a control portion 8.

Furthermore, a side collective lens 55 is arranged at a side of the flow cell 51, in a direction perpendicular to the optical axis extending linearly from the semiconductor laser light source 52 to the photodiode 54, and this side collective lens 55 is configured to collect lateral light (light emitted in a direction intersecting with the aforementioned optical axis) generated when emitting a laser beam to blood cells passing through the flow cell 51. A dichroic mirror 56 is provided on a downstream side of the side collective lens 55, and the dichroic mirror 56 is configured to divide signal light transmitted from the side collective lens 55 into a scattered light component and a fluorescent light component. A side scattered light photoreceptor photodiode 57 is provided at a side (a direction intersecting with a direction of an optical axis connecting the side collective lens 55 and the dichroic mirror 56) of the dichroic mirror 56, and an optical filter 58a and avalanche photodiode 58 are provided on an optical axis on a downstream side of the dichroic mirror 56. The side scattered light component separated by the dichroic mirror 56 is subjected to photoelectric conversion by the photodiode 57, and electrical signals (hereinafter referred to as side scattered light signals) generated by this conversion are transmitted to an amplifier 57a. The amplifier 57a is configured to amplify the transmitted side scattered light signals and output the amplified side scattered light signals to the control portion 8.

Furthermore, the side fluorescent light component is subjected to wavelength selection by the optical filter 58a, and subsequent photoelectric conversion by the avalanche photodiode 58, and electrical signals (side fluorescent light signals) generated by this are transmitted to an amplifier 58b. The amplifier 58b is configured to amplify the transmitted side fluorescent light signals and output the amplified side fluorescent light signals to the control portion 8.

Figure 8:
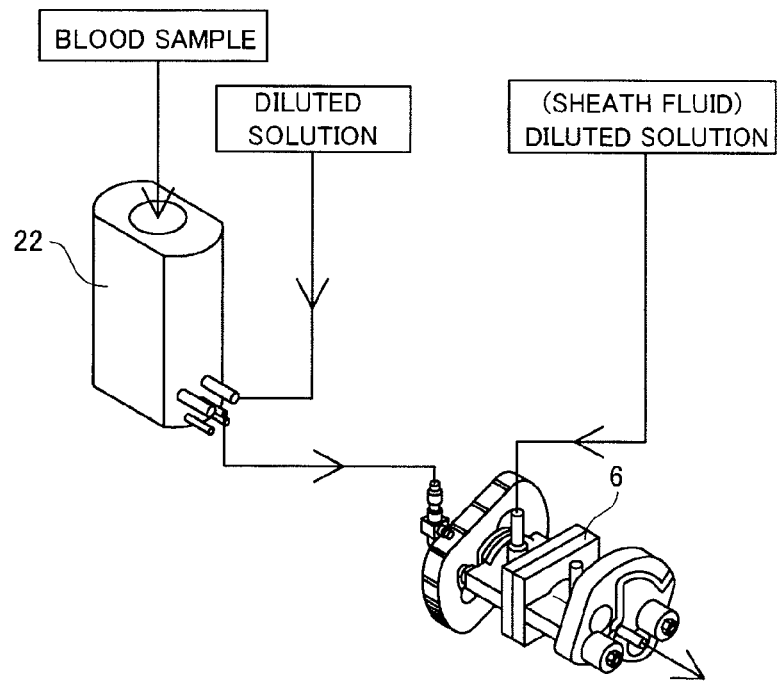
FIG. 8 is a perspective view schematically showing the structure of a DC measurement portion provided in the measurement unit of the blood analyzer according to the embodiment shown in FIG. 1.

The DC measurement portion 6 is configured to be capable of measuring a red blood cell count (RBC) and a platelet count (PLT) by a sheath flow DC detection method. The DC measurement portion 6 is configured to be capable of acquiring measurement data for calculating a hematocrit value (HCT) by a red-blood-cell pulse height detection method. Further, the DC measurement portion 6 is employed in detection of a white blood cell count (WBC) for calculating a lymphocyte ratio. The DC measurement portion 6 has a flow cell, and the measurement sample is transferred from the chamber 22 to the flow cell. When measuring a red blood cell count and a platelet count, for example, a measurement sample prepared by mixing the blood sample and the diluted solution in the chamber 22, along with the sheath fluid (diluted solution), is transferred from the sample supply portion 4 to the flow cell, as shown in FIG. 8. A fluid flow in a state where the measurement sample is surrounded by the sheath fluid (diluted solution) is formed in the flow cell.

Figure 9:
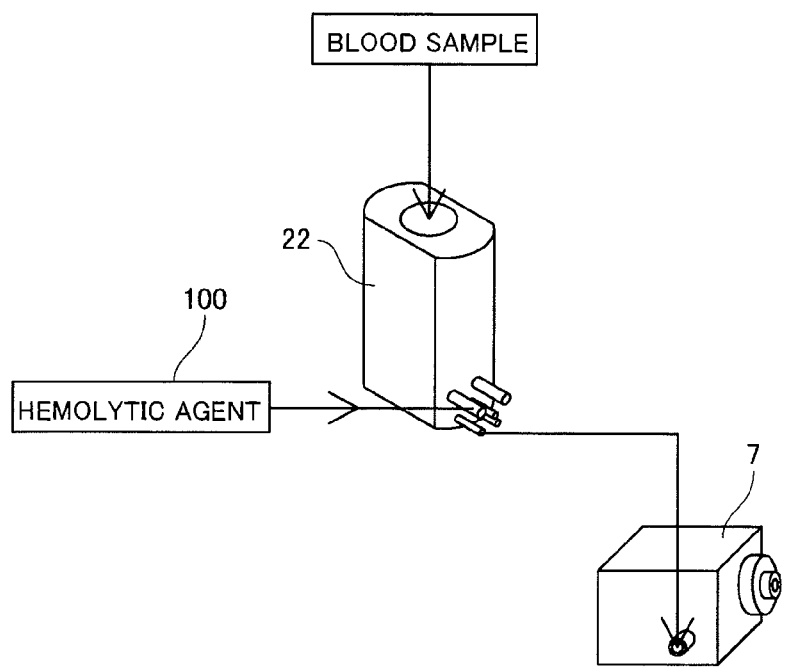
FIG. 9 is a perspective view schematically showing the structure of an HGB measurement portion provided in the measurement unit of the blood analyzer according to the embodiment shown in FIG. 1.

The HGB measurement portion 7 is configured to measure the amount of hemoglobin (HGB) by a methemoglobin method. The HGB measurement portion 7 has a cell storing a dilute sample, as shown in FIG. 9, and the measurement sample is transferred from the chamber 22 to this cell. The HGB measurement portion 7 has a light-emitting diode emitting light having a wavelength of about 555 nm and is configured to measure absorbance of the measurement sample by emitting the light from the light-emitting diode to the measurement sample in the aforementioned cell. When measuring hemoglobin, a measurement sample is prepared by mixing the blood sample, the diluted solution and the hemolytic agent 100 in the chamber 22.

The control portion 8 is constituted by a CPU, a ROM, a RAM, etc. and configured to control an operation of each part of the measurement unit 2.

The communication portion 9 is an RS-232C interface, a USB interface or an Ethernet (registered trademark) interface, for example and is configured to be capable of sending/receiving data to/from the data processing unit 3.

The data processing unit 3 is constituted by a computer comprising a CPU 31, a ROM 32, a RAM 33, a hard disk 34, a communication interface 35, an input portion 36 such as a keyboard and a mouse, and a display device 37, as shown in FIG. 2. An operating system, and an application program for analyzing the measurement data received from the measurement unit 2 are installed on the hard disk 34 of the data processing unit 3.

According to this embodiment, the CPU 31 of the data processing unit 3 is configured to analyze the measurement data and calculate a white blood cell count (WBC), a red blood cell count (RBC), a hemoglobin amount (HGB), a hematocrit value (HCT), a mean red blood cell volume (MCV), a mean red blood cell hemoglobin amount (MCH), a mean red blood cell hemoglobin concentration (MCHC), a platelet count (PLT) by executing this application program. Further, the CPU 31 is configured to prepare a scattergram employing the forward scattered light signals, the side scattered light signals and the side fluorescent light signals and classify the white blood cells into five groups of neutrophils (Neut), lymphocytes, monocytes (Mono), eosinophils (EO), and basophils (BASO).

The communication interface 35 is an RS-232C interface, a USB interface or an Ethernet (registered trademark) interface, for example and is configured to be capable of sending/receiving data to/from the measurement unit 2.

The hemolytic agent 100 according to this embodiment includes two types of cationic surfactants (lauryl trimethyl ammonium chloride; 34.1 mM, stearyl trimethyl ammonium chloride; 1.7 mM) but is free from a labeling substance, as shown in FIG. 10. This hemolytic agent 100 has a property in that hemoglobin in the blood is inverted to methemoglobin. Further, the hemolytic agent 100 contains a phosphate buffer solution to keep the pH about 5 to about 7. Thus, red blood cell membranes can be partially lysed so that a fluorescent dye described later can pass through the cell membranes in a state of holding a malarial parasite inside the red blood cells. As described later, each measurement sample employed in each measurement has a different dilution magnification of the hemolytic agent 100 and a different dilution magnification of the blood sample. The two types of cationic surfactants are employed as described above, whereby white blood cells in the measurement sample can be classified into four groups and malaria-infected red blood cells can be detected by simply varying the dilution magnification without employing more than one type of a hemolytic agent.

According to this embodiment, the staining fluid contains a fluorescent dye (Hoechst 34580 of Invitrogen, for example) having a structure of a chemical formula shown in FIG. 11 and one of a nonionic surfactant group substantially lysing a red blood cell membrane. Specifically, this fluorescent dye is a DNA-selective fluorescent dye, preferably a DNA-selective bisbenzimide type fluorescent dye. The DNA-selective fluorescent dye is a fluorescent dye staining preferentially DNA over RNA, and the DNA-selective bisbenzimide type fluorescent dye is a dye having a bisimide-based skeleton. In this way, red blood cells without a cell nucleus are not stained but DNA in malarial parasites is stained by employing the DNA-selective fluorescent dye, and hence malaria-infected red blood cells having a malarial parasite inside and others can be easily classified from a scattergram (see FIG. 17) obtained by the aforementioned flow cytometer. This fluorescent dye can be excited by the blue-violet laser beam (the wavelength is about 405 nm) emitted from the semiconductor laser light source 52.

Next, sample analysis processing in the blood analyzer 1 according to the embodiment of the present invention is described with reference to FIGS. 12 to 17.

First, when the blood analyzer 1 is started, the application program or the like is initialized, and thereafter the CPU 31 of the data processing unit 3 determines whether or not a measurement starting instruction from a user has been received at a step S1, and this determination is repeated until the instruction has been received. When the measurement starting instruction has been received, a measurement starting instruction signal is transmitted from the data processing unit 3 to the measurement unit 2 at a step S2.

Then, the control portion 8 of the measurement unit 2 determines whether or not the measurement starting instruction signal has been received at a step S21, and this determination is repeated until the signal has been received. When the measurement unit 2 has received the measurement starting instruction signal, the blood sample is suctioned from the blood collection tube 20 set on the blood collection tube set portion 2a by the pipette 21 at a step S22.

Figure 13:
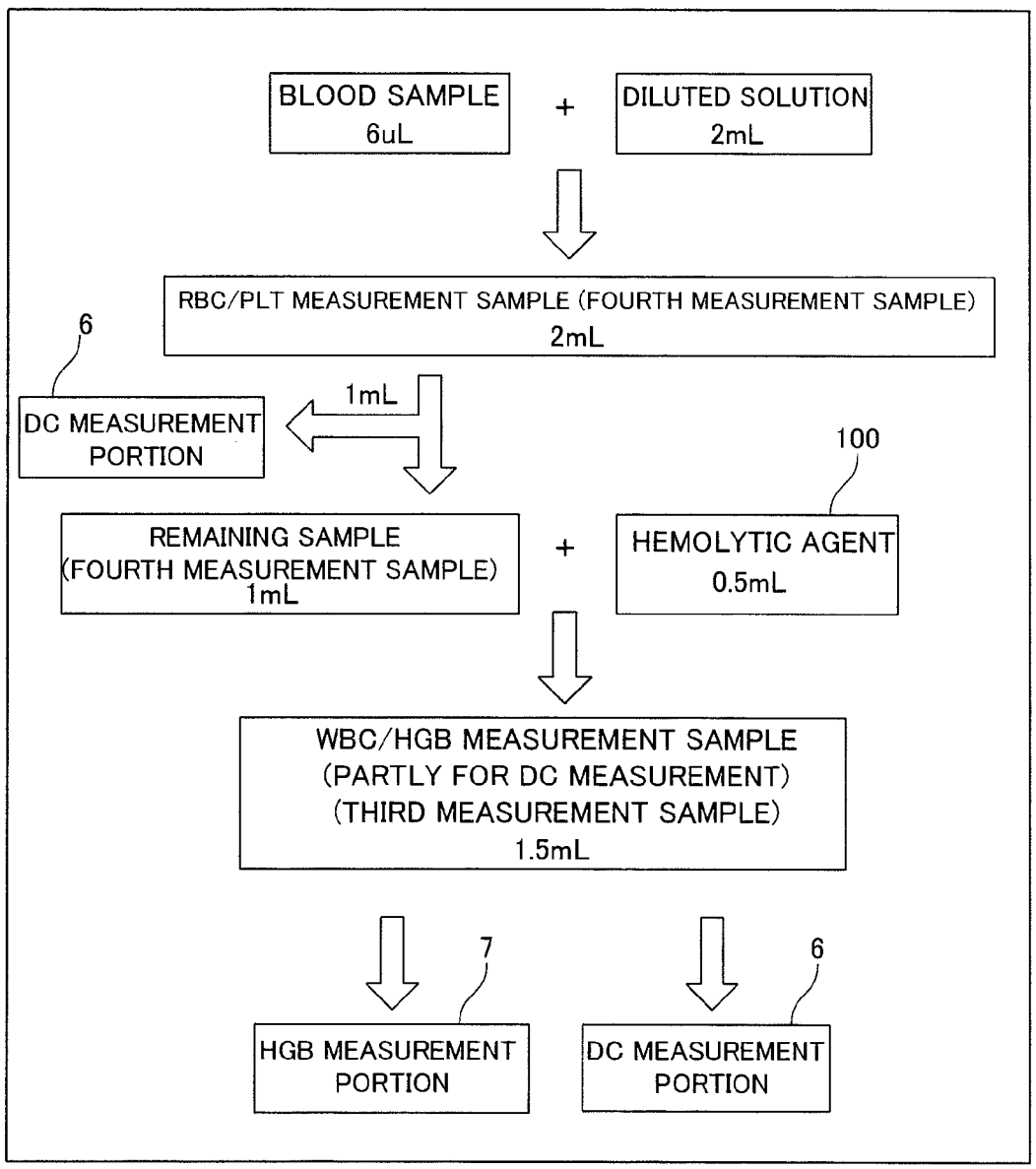
FIG. 13 is a diagram for illustrating a step of preparing a third measurement sample and a fourth measurement sample employed in the blood analyzer according to the embodiment shown in FIG. 1.

At a step S23, an RBC/PLT measurement sample (hereinafter referred to as the fourth measurement sample) is prepared by the sample supply portion 4. More specifically, a predetermined quantity (2.0 mL, for example) of the diluted solution from the diluted solution container 24 and a predetermined quantity (6 µL, for example) of the blood sample suctioned from the blood collection tube 20 by the pipette 21 are supplied to the chamber 22 and stirred, as shown in FIG. 13. Thus, a predetermined quantity (2.0 mL, for example) of the fourth measurement sample is prepared. Thereafter, a part (1 mL, for example) of the fourth measurement sample in the chamber 22, along with the sheath fluid (diluted solution), is transferred to the DC measurement portion 6 and the DC measurement portion 6 detects the RBC and the PLT of the fourth measurement sample at a step S24.

Then, at a step S25, a WBC/HGB measurement sample (partly for DC detection) (hereinafter referred to as the third measurement sample) is prepared by the sample supply portion 4. More specifically, a predetermined quantity (0.5 mL, for example) of the hemolytic agent 100 is supplied from the hemolytic agent container 25 to the chamber 22 in which a predetermined quantity (1 mL, for example) of the fourth measurement sample remains and stirred, as shown in FIG. 13. In other words, after the blood sample and the diluted solution are mixed in the chamber 22, the hemolytic agent 100 is mixed to prepare the third measurement sample. Thus, the third measurement sample in which the hemolytic agent 100 is diluted by 3 times (hemolytic agent/diluted solution=1/2) and the blood sample is diluted by 500 times is prepared. Thus, the red blood cells are hemolyzed, and the hemoglobin is inverted to methemoglobin. Thereafter, at a step S26, the third measurement sample in the chamber 22 is transferred to the DC measurement portion 6, and the WBC in the third measurement sample is measured. At a step S27, the third measurement sample is transferred to the HGB measurement portion 7, and the HGB of the third measurement sample is detected.

At a step S28, a WBC measurement sample (for classification) (hereinafter referred to as the first measurement sample) is prepared by the sample supply portion 4. More specifically, a predetermined quantity (1 mL, for example) of a diluted hemolytic agent obtained by diluting the same hemolytic agent 100 as that contained in the aforementioned third measurement sample by 25 times (hemolytic agent/diluted solution=1/24) and a predetermined quantity (10 µL, for example) of the blood sample suctioned from the blood collection tube 20 are supplied to the chamber 23 and stirred. Thus, the first measurement sample in which the blood sample is diluted by 100 times is prepared. Thereafter, the first measurement sample in the chamber 23, along with the sheath fluid (diluted solution), is transferred to the WBC classification measurement portion 5 and the WBC classification measurement portion 5 detects the WBC in the first measurement sample at a step S29.

According to this embodiment, at a step S30, a malaria measurement sample (hereinafter referred to as the second measurement sample) is prepared by the sample supply portion 4. More specifically, a predetermined quantity (1 mL, for example) of a diluted hemolytic agent obtained by diluting the same hemolytic agent 100 as that contained in the aforementioned first measurement sample by 9 times (hemolytic agent/diluted solution=1/8), a predetermined quantity (10 µL, for example) of the blood sample suctioned from the blood collection tube 20 and a predetermined quantity (10 µL, for example) of the staining fluid from the staining fluid container 26 are supplied to the chamber 23 and stirred. In other words, the blood sample and the staining fluid are mixed with each other in a state where the hemolytic agent 100 and the diluted solution are mixed with each other in the chamber 23. Thus, the hemolytic agent 100 is mixed with the blood sample in a state of being diluted with the diluted solution, and hence the blood sample can be inhibited from being mixed with the hemolytic agent having a concentration higher than a desired concentration. Then, the second measurement sample in which the blood sample is diluted by 100 times is prepared. In this way, a dilution magnification (9 times) of the hemolytic agent 100 in the second measurement sample is rendered smaller than a dilution magnification (25 times) of the hemolytic agent 100 in the first measurement sample, whereby the red blood cells in the measurement sample can be moderately hemolyzed, and hence malaria-infected red blood cells can be accurately detected. Thus, both the first measurement sample and the second measurement sample can be prepared employing the common hemolytic agent 100 stored in the hemolytic agent container 25. Thereafter, the second measurement sample in the chamber 23, along with the sheath fluid (diluted solution), is transferred to the WBC classification measurement portion 5 and the WBC classification measurement portion 5 detects malaria in the second measurement sample at a step S31. At a step S32, measurement data obtained by measurement in each detection portion is transmitted from the measurement unit 2 to the data processing unit 3.

Figure 14:
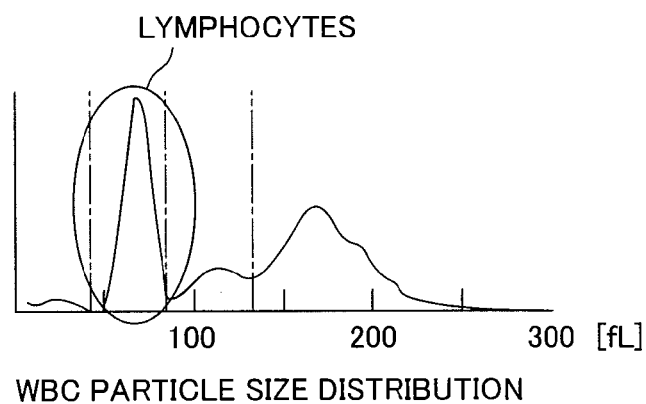
FIG. 14 is a particle size distribution chart of white blood cells prepared in the blood analyzer according to the embodiment shown in FIG. 1.

The data processing unit 3 determines whether or not the measurement data transmitted from the measurement unit 2 has been received at a step S3, and this determination is repeated until the measurement data has been received. When the measurement data has been received, at a step S4, the CPU 31 calculates the white blood cell count (WBC) on the basis of the measurement data obtained by the WBC detection, measured at the step S26. At a step S5, the CPU 31 prepares a particle size distribution chart of the white blood cells on the basis of the measurement data obtained by the WBC detection, as shown in FIG. 14 and calculates the ratio of the lymphocytes to the white blood cell count (WBC). The lymphocyte appears as a first peak (group) from the left in the particle size distribution chart.

Figure 15:
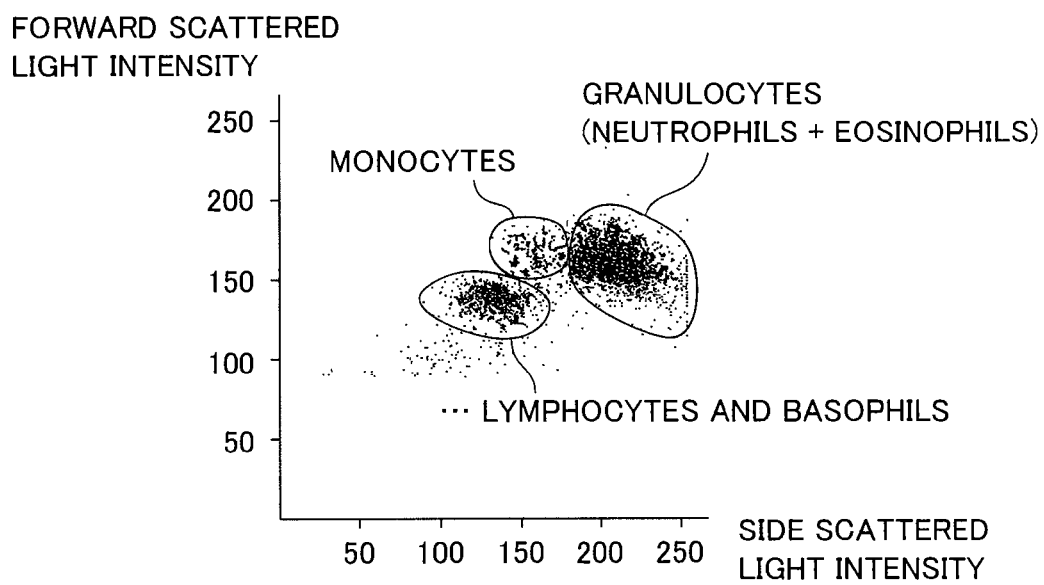
FIG. 15 is a scattergram for classification of white blood cells prepared in the blood analyzer according to the embodiment shown in FIG. 1.
Figure 22:
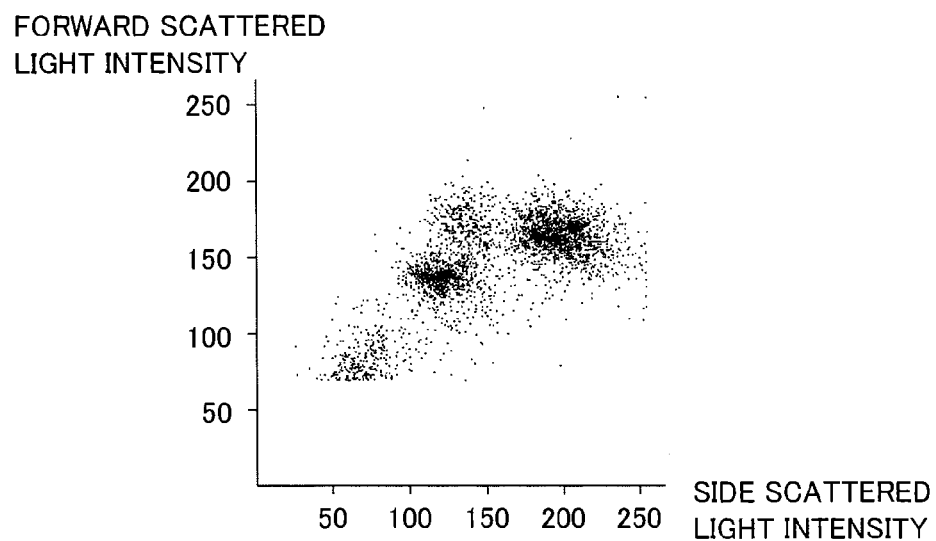
FIG. 22 is a diagram showing an experimental result when employing the hemolytic agent shown in FIG. 10 in the blood analyzer according to the embodiment shown in FIG. 1.

Then, at a step S6, the CPU 31 classifies the white blood cells into three groups of a group of lymphocytes and basophils, monocytes and granulocytes (a group of neutrophils and eosinophils) on the basis of the measurement data obtained by the WBC classification and detection, measured at the step S29. More specifically, the CPU 31 prepares a scattergram, employing the forward scattered light signals and the side scattered light signals, as shown in FIG. 15 and calculates ratios of a group of lymphocytes and basophils, monocytes and granulocytes (a group of neutrophils and eosinophils) to the white blood cell count (WBC) from this scattergram. FIG. 22 shows a scattergram by a forward scattered light signal and a side scattered light signal obtained by measuring a blood sample actually collected from a subject employing the hemolytic agent (see FIG. 10) in this embodiment. As shown in FIG. 22, it is also understood from an actual measurement result that the white blood cells can be classified into three groups of a group of lymphocytes and basophils, monocytes and granulocytes (a group of neutrophils and eosinophils) on the scattergram.

Figure 16:
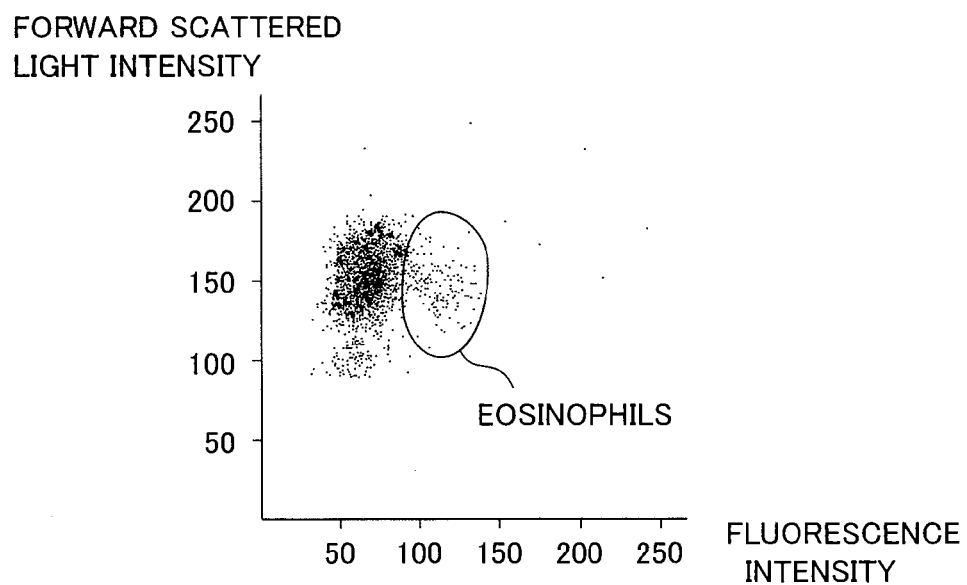
FIG. 16 is a scattergram for classification of white blood cells prepared in the blood analyzer according to the embodiment shown in FIG. 1.
Figure 23:
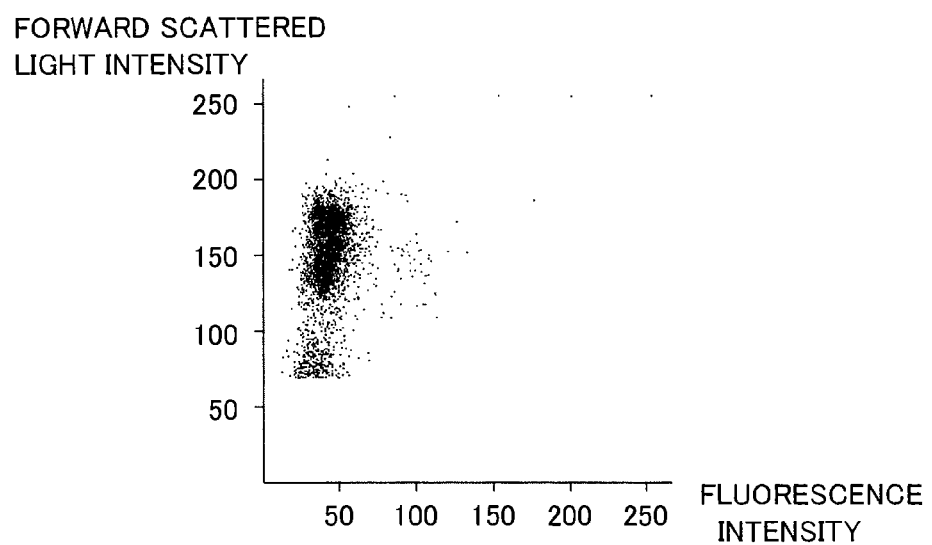
FIG. 23 is a diagram showing an experimental result when employing the hemolytic agent shown in FIG. 10 in the blood analyzer according to the embodiment shown in FIG. 1.

At a step S7, the CPU 31 classifies the white blood cells into two groups of eosinophils and the others on the basis of the measurement data obtained by the WBC classification and detection. More specifically, the CPU 31 prepares a scattergram, employing the forward scattered light signals and the side fluorescent light signals, as shown in FIG. 16 and calculates a ratio of the eosinophils to the white blood cell count (WBC) from this scattergram. These side fluorescent light signals are based on intrinsic fluorescence of the white blood cells excited by the blue-violet semiconductor laser beam (the wavelength is about 405 nm) emitted from the semiconductor laser light source 52, and the eosinophils have a stronger fluorescence intensity than the others in the white blood cells. The CPU 31 can also calculate the ratio of the eosinophils to the white blood cell count (WBC) from a scattergram obtained by employing the side scattered light signals and the side fluorescent light signals. FIG. 23 shows a scattergram by the forward scattered light signal and a side fluorescent light signal obtained by measuring the blood sample actually collected from the subject employing the hemolytic agent (see FIG. 10) in this embodiment. As shown in FIG. 23, it is also understood from an actual measurement result that the white blood cells can be classified into the eosinophils and the others on the scattergram.

Thereafter, at a step S8, the CPU 31 calculates a ratio of the neutrophils to the white blood cell count (WBC) by subtracting the ratio of the eosinophils calculated at the step S7 from the ratio of the granulocytes (a group of neutrophils and eosinophils) calculated at the step S6. Thus, the white blood cells are classified into four groups of the group of lymphocytes and basophils, the monocytes, the neutrophils and the eosinophils. At a step S9, the CPU 31 calculates a ratio of the basophils to the white blood cell count (WBC) by subtracting the ratio of the lymphocytes calculated at the step S5 from the ratio of the group of lymphocytes and basophils. Thus, the white blood cells are classified into five groups of the lymphocytes, the basophils, the monocytes, the neutrophils and the eosinophils.

Figure 17:
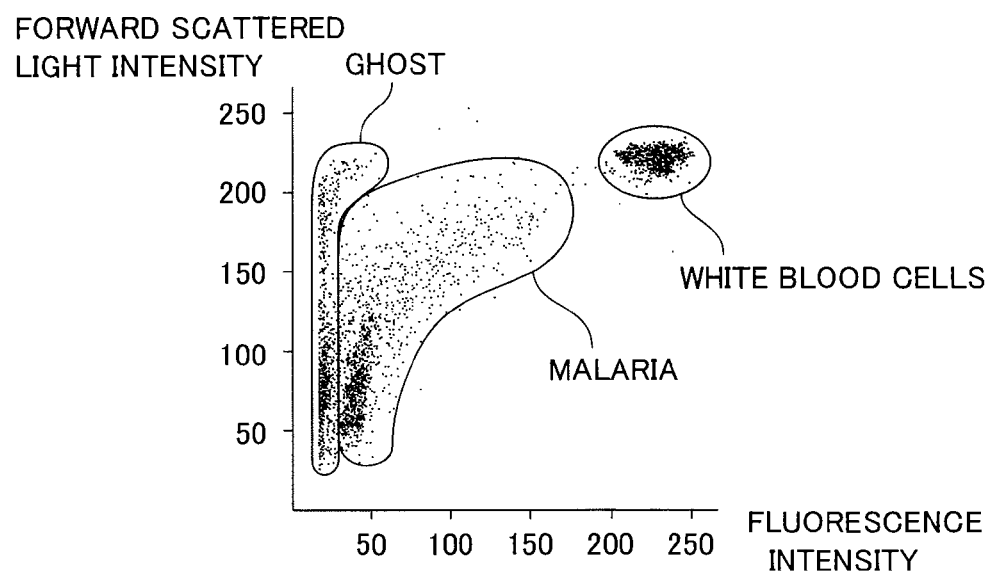
FIG. 17 is a scattergram for classification of malaria prepared in the blood analyzer according to the embodiment shown in FIG. 1.

According to this embodiment, at a step S10, the CPU 31 separates the malaria-infected red blood cells from the others on the basis of the measurement data obtained by the malaria detection, measured at the step S31. Specifically, the CPU 31 prepares a scattergram, employing the forward scattered light signals and the side fluorescent light signals, as shown in FIG. 17 and separates the malaria-infected red blood cells from the others from this scattergram. More specifically, malaria-negative red blood cells appear in an area where a fluorescence intensity is small whereas the malaria-infected red blood cells appear in an area where the fluorescence intensity is relatively large on the scattergram in FIG. 17. Further, the white blood cells appear in an area where both the fluorescence intensity and a scattered light intensity are large due to the size and the amount of DNA thereof. Thus, the presence of malaria infection can be determined.

Then, at a step S11, the CPU 31 calculates the red blood cell count (RBC), the platelet count (PLT) and the hematocrit value (HCT) on the basis of the measurement data obtained by the RBC/PLT detection, measured at the step S24.

At a step S12, the CPU 31 calculates the amount of the hemoglobin (HGB) on the basis of the measurement data obtained by the HGB detection, measured at the step S27. In other words, a hemoglobin concentration is calculated on the basis of the absorbance obtained by HGB detection employing an SLS hemoglobin method. Thus, the hemoglobin concentration can be acquired employing the third measurement sample identical to the measurement sample employed to classify the white blood cells into five groups (neutrophils, lymphocytes, monocytes, eosinophils and basophils).

Thereafter, at a step S13, the CPU 31 calculates the mean red blood cell volume (MCV), the mean red blood cell hemoglobin amount (MCH) and the mean red blood cell hemoglobin concentration (MCHC) from the red blood cell count (RBC), the hematocrit value (HCT) and the amount of the hemoglobin (HGB).

The formula for calculating each value is expressed by the following formulas (1) to (3):

$$MCV = (HCT/RBC) \times 1000 \qquad (1)$$

In the aforementioned formula (1), MCV represents a mean red blood cell volume (fL), HCT represents a hematocrit value (%) and RBC represents a red blood cell count $(\times 10^4/\mu L)$.

$$MCH = (HGB/RBC) \times 1000 \qquad (2)$$

In the aforementioned formula (2), MCH represents a mean red blood cell hemoglobin amount (pg), HGB represents the amount of hemoglobin (g/dL) and RBC represents a red blood cell count ($\times 10^4/\mu L$).

$$MCHC=(HGB/HCT)\times 100 \qquad (3)$$

In the aforementioned formula (3), MCHC represents a mean red blood cell hemoglobin concentration (g/dL), HGB represents the amount of hemoglobin (g/dL) and HCT represents a hematocrit value (%).

At a step S14, calculation results of the white blood cell count (WBC), the red blood cell count (RBC), the amount of the hemoglobin (HGB), the hematocrit value (HCT), the mean red blood cell volume (MCV), the mean red blood cell hemoglobin amount (MCH), the mean red blood cell hemoglobin concentration (MCHC) and the platelet count (PLT) calculated as described above are output to the display device 37. Further, the ratios of the neutrophils, the lymphocytes, the monocytes, the eosinophils and the basophils to the white blood cell count (WBC) are output to the display device 37, and the result of detection of malaria is also output. In addition to the ratio of each blood cell to the white blood cell count (WBC), the white blood cell count (WBC) and the neutrophil count, the lymphocyte count, the monocyte count, the eosinophil count and the basophil count calculated on the basis of the ratio of each blood cell are output.

Thereafter, at a step S15, the presence of a shutdown instruction from the user is determined, and when the shutdown instruction has not been received, the CPU 31 moves to the step S1. When the shutdown instruction has been received, an operation of the data processing unit 3 of the sample analysis processing in the blood analyzer 1 is terminated. In the measurement unit 2, after the measurement data is transmitted to the data processing unit 3 at the step S32, whether or not a shutdown instruction from the user has been received is determined at a step S33. When the shutdown instruction has not been received, the control portion 8 moves to the step S21. When the shutdown instruction has been received, an operation of the measurement unit 2 of the sample analysis processing in the blood analyzer 1 is terminated.

According to this embodiment, as hereinabove described, the CPU 31 classifying the white blood cells in the first measurement sample into at least four groups of the monocytes, the neutrophils, the eosinophils and the others on the basis of the side fluorescent light signals, the forward scattered light signals and the side scattered light signals generated from the first measurement sample containing the blood sample and the hemolytic agent 100 by the WBC classification measurement portion 5 and classifying the blood cells in the second measurement sample into the malaria-infected red blood cells and the others on the basis of the side fluorescent light signals and the forward scattered light signals generated from the second measurement sample containing the blood sample, the same hemolytic agent 100 as the aforementioned hemolytic agent 100 and the staining agent by the WBC classification measurement portion 5 is provided, whereby the hemolytic agent for classifying the white blood cells into four groups and the hemolytic agent for detecting the malaria-infected red blood cells can be rendered common, and hence it is not necessary to develop two types of reagents (hemolytic agents) having different compositions to classify the white blood cells and detect the malaria-infected red blood cells. Thus, the white blood cells in the measurement sample can be classified into four groups and the malaria-infected red blood cells can be detected while reducing a burden on the user due to the development of the reagent.

According to this embodiment, the CPU 31 is configured to classify the white blood cells in the third measurement sample into the lymphocytes and the others on the basis of the measurement data obtained by the DC measurement portion 6 and classify the white blood cells in the measurement sample into at least five groups of the lymphocytes, the basophils, the monocytes, the neutrophils and the eosinophils on the basis of this classification result and the aforementioned classification result of the four groups of the white blood cells, whereby the white blood cells can be classified into the lymphocytes and the others employing the same hemolytic agent 100 as the hemolytic agent for classifying the white blood cells and detecting the malaria-infected red blood cells, and hence the white blood cells can be classified into five groups without developing a hemolytic agent having a different composition separately.

In the blood analysis method according to this embodiment, as hereinabove described, the step of classifying the white blood cells in the first measurement sample into at least four groups of the monocytes, the neutrophils, the eosinophils, the others on the basis of the side fluorescent light signals, the forward scattered light signals and the side scattered light signals generated from the first measurement sample containing the blood sample and the hemolytic agent 100 by the WBC classification measurement portion 5 and the step of classifying the blood cells in the second measurement sample into the malaria-infected red blood cells and the others on the basis of the side fluorescent light signals and the forward scattered light signals generated from the second measurement sample containing the blood sample, the same hemolytic agent 100 as the aforementioned hemolytic agent 100 and the staining agent by the WBC classification measurement portion 5 are provided, whereby the hemolytic agent for classifying the white blood cells into four groups and the hemolytic agent for detecting the malaria-infected red blood cells can be rendered common, and hence it is not necessary to develop two types of reagents (hemolytic agents) having different compositions to classify the white blood cells and detect the malaria-infected red blood cells. Thus, the white blood cells in the measurement sample can be classified into four groups and the malaria-infected red blood cells can be detected while reducing a burden on the user due to the development of the reagent.

The hemolytic agent according to this embodiment is employed in the blood analysis method comprising the step of classifying the white blood cells in the first measurement sample into at least four groups of the monocytes, the neutrophils, the eosinophils, the others on the basis of the side fluorescent light signals, the forward scattered light signals and the side scattered light signals generated from the first measurement sample containing the blood sample and the hemolytic agent 100 by the WBC classification measurement portion 5 and the step of classifying the blood cells in the second measurement sample into the malaria-infected red blood cells and the others on the basis of the side fluorescent light signals and the forward scattered light signals generated from the second measurement sample containing the blood sample, the same hemolytic agent 100 as the aforementioned hemolytic agent 100 and the staining agent by the WBC classification measurement portion 5, as hereinabove described, whereby the hemolytic agent for classifying the white blood cells into four groups and the hemolytic agent for detecting the malaria-infected red blood cells can be rendered common, and hence it is not necessary to develop two types of reagents (hemolytic agents) having different compositions to classify the white blood cells and detect the malaria-infected red blood cells. Thus, the white blood cells in the measurement sample can be classified into four groups and the malaria-infected red blood cells can be detected while reducing a burden on the user due to the development of the reagent.

The staining agent according to this embodiment is employed in the blood analysis method comprising the step of classifying the white blood cells in the first measurement sample into at least four groups of the monocytes, the neutrophils, the eosinophils, the others on the basis of the side fluorescent light signals, the forward scattered light signals and the side scattered light signals generated from the first measurement sample containing the blood sample and the hemolytic agent 100 by the WBC classification measurement portion 5 and the step of classifying the blood cells in the second measurement sample into the malaria-infected red blood cells and the others on the basis of the side fluorescent light signals and the forward scattered light signals generated from the second measurement sample containing the blood sample, the same hemolytic agent 100 as the aforementioned hemolytic agent 100 and the staining agent by the WBC classification measurement portion 5, as hereinabove described, whereby the hemolytic agent for classifying the white blood cells into four groups and the hemolytic agent for detecting the malaria-infected red blood cells can be rendered common, and hence it is not necessary to develop two types of reagents (hemolytic agents) having different compositions to classify the white blood cells and detect the malaria-infected red blood cells. Thus, the white blood cells in the measurement sample can be classified into four groups and the malaria-infected red blood cells can be detected while reducing a burden on the user due to the development of the reagent.

EXAMPLE

Next, relationships between malaria infection rates obtained by visual observation and malaria infection rates obtained on the basis of the method (employing a reagent similar to that described in the aforementioned embodiment) described in the aforementioned embodiment are shown in the following Table 1. Measurement by the visual observation and measurement by the method described in the aforementioned embodiment are performed with respect to the same specimen in a plurality of blood samples.

TABLE 1

|  | VISUAL OBSERVATION (%) | METHOD OF EMBODIMENT (%) |
| --- | --- | --- |
| SAMPLE 1 | 0.01 | 0.01 |
| SAMPLE 2 | 0.03 | 0.03 |
| SAMPLE 3 | 0.08 | 0.06 |
| SAMPLE 4 | 0.17 | 0.13 |

As shown in Table 1, the malaria infection rates obtained by the visual observation and the malaria infection rates obtained on the basis of the method described in the aforementioned embodiment are substantially identical to each other, and according to the method described in the aforementioned embodiment, it could be confirmed that malaria-infected red blood cells could be accurately detected.

The malaria infection rates by the visual observation were calculated by the following formula (4).

$$\text{Malaria infection rate (\%)} = X/Y \times 100 \quad (4)$$

In the aforementioned formula (4), X represents the number of red blood cells determined to have been infected by malaria of a predetermined number ($=Y$) of red blood cells counted by the visual observation, and Y represents the aforementioned predetermined number. In the Table 1, Y is about 10,000 with respect to Samples 1 and 2, about 20,000 with respect to Sample 3 and about 30,000 with respect to Sample 4.

The malaria infection rates obtained on the basis of the method described in the aforementioned embodiment were calculated by the following formula (5).

$$\text{Malaria infection rate (\%)} = (6)/(7) \times 100 \quad (5)$$

In the aforementioned formula (5), (6) represents $A \times B/C$, and (7) represents the number of red blood cells obtained by measuring the same blood sample by a multiparameter automated hematology analyzer Model XE-2100 (SYSMEX CORPORATION). A of the aforementioned (6) is the number of blood cells in a malaria area in FIG. 17, B of the aforementioned (6) is the number of white blood cells obtained by measuring the same blood sample by the multiparameter automated hematology analyzer Model XE-2100 and C of the aforementioned (6) is the number of blood cells in a white blood cell area in FIG. 17.

The embodiment disclosed this time must be considered as illustrative in all points and not restrictive. The range of the present invention is shown not by the above description of the embodiment but by the scope of claims for patent, and all modifications within the meaning and range equivalent to the scope of claims for patent are further included.

For example, while the example of connecting the single hemolytic agent container serving as a reagent container, storing the hemolytic agent commonly employed in the WBC detection, the HGB detection, the WBC classification detection and the malaria detection to the sample supply portion has been shown in the aforementioned embodiment, the present invention is not restricted to this, but four hemolytic agent containers may be connected to the sample supply portion so as to store the hemolytic agents employed in the respective detections separately, or a hemolytic agent employed in any of the aforementioned four detections may be stored in a common hemolytic agent container and two or three hemolytic agent containers may be connected to the sample supply portion. Alternatively, more than four hemolytic agent containers may be connected to the sample supply portion. At this time, if the hemolytic agents stored in the respective hemolytic agent containers are diluted by respective predetermined dilution magnifications, no steps to dilute the hemolytic agents by desired dilution magnifications may be provided separately when preparing the measurement samples employed in the respective detections.

While the hemolytic agent free from a labeling substance has been shown as an example of a hemolytic agent in the aforementioned embodiment, the present invention is not restricted to this, but the hemolytic agent may contain a labeling substance.

While the example of employing the same hemolytic agent as that employed in the WBC classification detection for the WBC detection and the HGB detection has been shown in the aforementioned embodiment, the present invention is not restricted to this, but different dedicated hemolytic agents may be employed in the respective WBC detection, HGB detection and WBC classification detection.

While the example of performing each detection processing in the order of the RBC/PLT detection, the WBC detection, the HGB detection, the WBC classification detection and the malaria detection from the earliest in the sample analysis processing has been shown in the aforementioned embodiment, the present invention is not restricted to this, but each detection processing may be performed in another order other than the aforementioned order in the sample analysis processing. Also, the order of white blood cell classification processing, malaria classification processing, red blood cell count/platelet count calculation processing and hemoglobin amount calculation processing in the sample analysis processing can be properly varied.

While the example of providing the semiconductor laser light source having the blue-violet semiconductor laser element has been shown in the aforementioned embodiment, the present invention is not restricted to this, but a light source having another laser element other than the blue-violet semiconductor laser element, such as a blue semiconductor laser element or an argon laser element may be provided.

While the example of the structure diluting the hemolytic agent in the second measurement sample by 9 times has been shown in the aforementioned embodiment, the present invention is not restricted to this. The hemolytic agent in the second measurement sample is preferably diluted by at least 9 times and not more than 12 times.

While the hemolytic agent including the cationic surfactant (lauryl trimethyl ammonium chloride; 34.1 mM, stearyl trimethyl ammonium chloride; 1.7 mM), which is an alkyl trimethyl ammonium salt and the number of carbons of the alkyl group of which is at least twelve and not more than eighteen, has been shown as an example of a hemolytic agent in the aforementioned embodiment, the present invention is not restricted to this, but a hemolytic agent including a cationic surfactant having a concentration other than the aforementioned concentration may be employed so far as a concentration of the cationic surfactant (the total of lauryl trimethyl ammonium chloride and stearyl trimethyl ammonium chloride in the aforementioned embodiment) in the WBC measurement sample (for classification) is at least 0.62 mM and not more than 2.15 mM. According to the aforementioned embodiment, the measurement sample is prepared by diluting the hemolytic agent by 25 times, and hence a concentration of the cationic surfactant in the hemolytic agent is 15.5 nM when the concentration of the cationic surfactant in the WBC measurement sample (for classification) is 0.62 mM, and the concentration of the cationic surfactant in the hemolytic agent is 53.75 nM when the concentration of the cationic surfactant in the WBC measurement sample (for classification) is 2.15 mM. If a cationic surfactant, the number of carbons of the alkyl group of which is at least eight and not more than ten is employed instead of the aforementioned hemolytic agent, the measurement sample can be measured even when a concentration of the cationic surfactant in the WBC measurement sample (for classification) is 2.15 mM or more.

Experimental results when fluctuating the concentration of the cationic surfactant in the hemolytic agent in the blood analyzer according to the embodiment of the present invention are described. In the experiment, a plurality of experimental results in which the concentrations of the cationic surfactants in the hemolytic agents are slightly different from each other have been obtained, but here two experimental results when the hemolytic agent in which the concentration of the cationic surfactant in the WBC measurement sample (for classification) is 2.15 mM is employed and when the hemolytic agent in which the concentration of the cationic surfactant in the WBC measurement sample (for classification) is 0.62 mM is employed are described on behalf of the plurality of experimental results.

Figure 18:
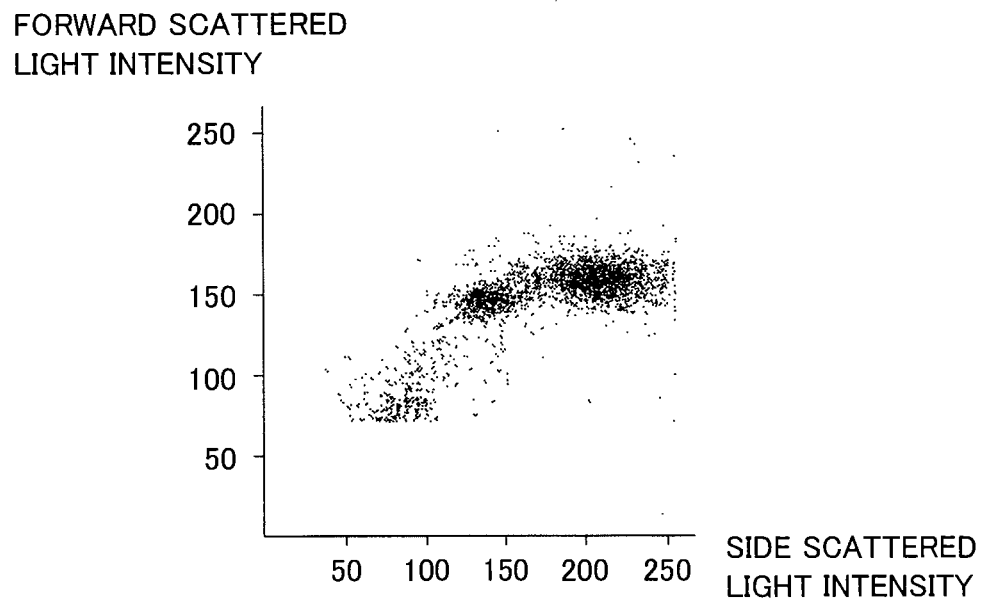
FIG. 18 is a diagram showing an experimental result when employing a hemolytic agent in which a concentration of a cationic surfactant in a WBC measurement sample (for classification) is 2.15 mM in the blood analyzer according to the embodiment shown in FIG. 1.
Figure 19:
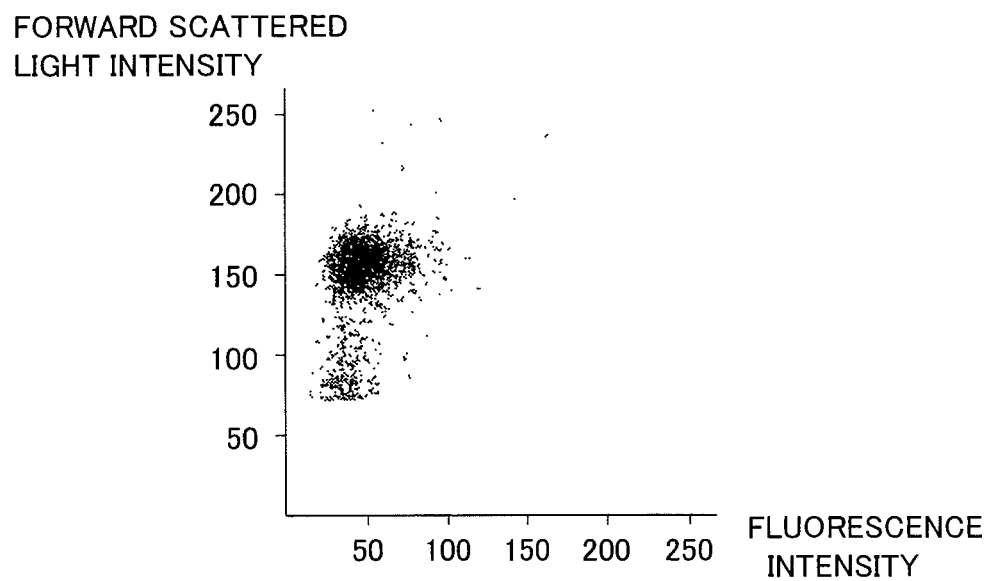
FIG. 19 is a diagram showing an experimental result when employing a hemolytic agent in which a concentration of a cationic surfactant in the WBC measurement sample (for classification) is 2.15 mM in the blood analyzer according to the embodiment shown in FIG. 1.
Figure 20:
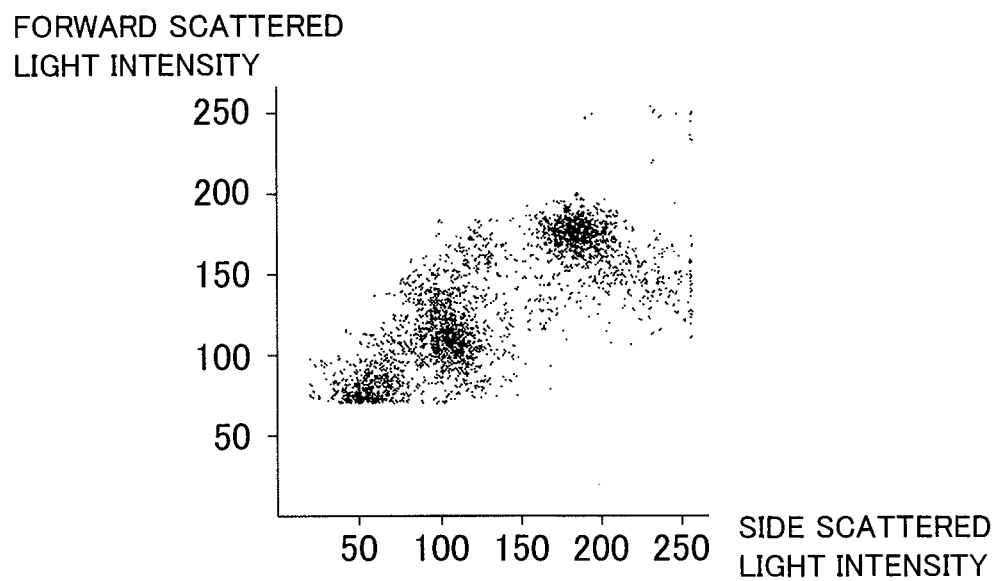
FIG. 20 is a diagram showing an experimental result when employing a hemolytic agent in which a concentration of a cationic surfactant in the WBC measurement sample (for classification) is 0.62 mM in the blood analyzer according to the embodiment shown in FIG. 1.
Figure 21:
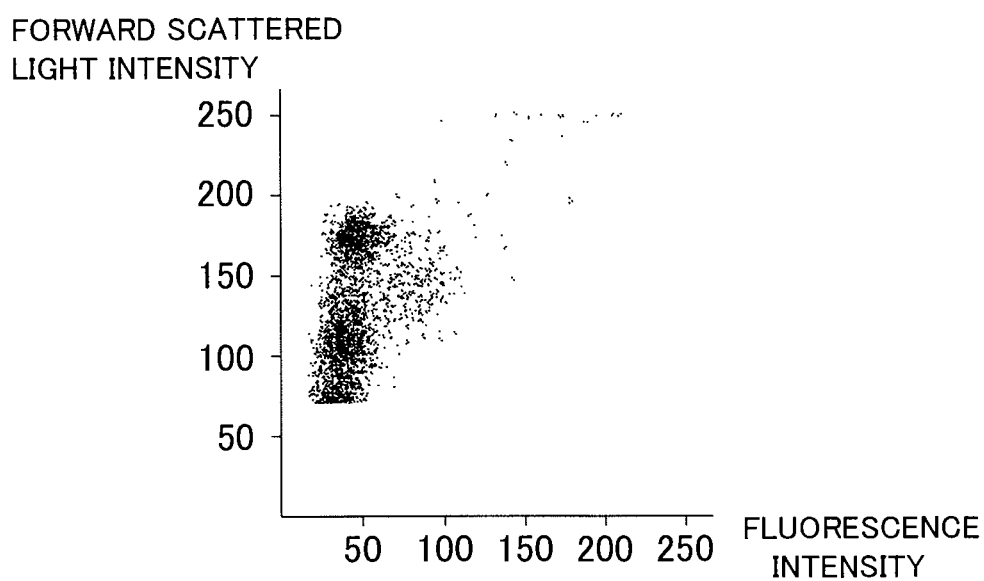
FIG. 21 is a diagram showing an experimental result when employing a hemolytic agent in which a concentration of a cationic surfactant in the WBC measurement sample (for classification) is 0.62 mM in the blood analyzer according to the embodiment shown in FIG. 1.

As shown in FIGS. 18 and 20, the white blood cells can be classified into three groups of the group of lymphocytes and basophils, the monocytes and the granulocytes (the group of neutrophils and eosinophils) on the scattergram. As shown in FIGS. 19 and 21, the white blood cells can be classified into the eosinophils and the others on the scattergram. Further, the white blood cells can be classified into four groups of the group of lymphocytes and basophils, the monocytes, the neutrophils and the eosinophils from these classification results. Therefore, the white blood cells can be conceivably classified into four groups in a case where the concentration of the cationic surfactant in the WBC measurement sample (for classification) is in the range of at least 0.62 mM and not more than 2.15 mM.

What is claimed is:
1. A blood analyzer comprising:
   a sample preparation portion configured to prepare a first measurement sample and a second measurement sample;
   a light information generation portion configured to generate first fluorescent information and at least two types of first scattered light information from said first measurement sample and to generate second fluorescent information and second scattered light information from said second measurement sample; and
   a control portion configured to
      instruct the sample preparation portion to prepare the first measurement sample by mixing a first aliquot of a blood sample and first aliquot of a hemolytic agent, and to prepare the second measurement sample by mixing a second aliquot of said blood sample, a second aliquot of said hemolytic agent, and a staining agent,
      perform a first classification of white blood cells in said first measurement sample into at least four groups comprising monocytes, neutrophils, eosinophils and others on the basis of said first fluorescent information and said two types of first scattered light information generated by said light information generation portion, and
      classify blood cells in said second measurement sample into at least malaria-infected red blood cells and others on the basis of said second fluorescent information and said second scattered light information generated by said light information generation portion,
   wherein
      said sample preparation portion is further configured to prepare a third measurement sample,
      said blood analyzer further comprising an electrical information generation portion configured to generate electrical information of a sample from said third measurement sample, and wherein
      said control portion is configured to perform a second classification of white blood cells in said third measurement sample into at least lymphocytes and others on the basis of said electrical information generated by said electrical information generation portion and classify white blood cells in said measurement samples into at least five groups comprising lympho- cytes, basophils, monocytes, neutrophils and eosinophils on the basis of classification results of said first classification and said second classification.

2. The blood analyzer according to claim 1, further comprising a second light information generation portion configured to generate at least either transmitted light information or scattered light information of a sample from said third measurement sample, wherein
said control portion is configured to acquire a hemoglobin concentration in said third measurement sample on the basis of at least either said transmitted light information or said scattered light information generated by said second light information generation portion.

3. The blood analyzer according to claim 1, wherein
the control portion is configured to instruct the sample preparation portion to prepare the measurement samples such that a dilution magnification of said hemolytic agent in said second measurement sample is different from a dilution magnification of said hemolytic agent in said first measurement sample.

4. The blood analyzer according to claim 1, wherein
said sample preparation portion is configured to prepare said first measurement sample by mixing said blood sample, said hemolytic agent stored in a predetermined reagent container and a predetermined quantity of diluted solution, and to prepare said second measurement sample by mixing said blood sample, said hemolytic agent stored in said predetermined reagent container and a quantity of said diluted solution smaller than said predetermined quantity.

5. The blood analyzer according to claim 4, wherein
said sample preparation portion is configured to prepare said second measurement sample by mixing said blood sample in a state of mixing said hemolytic agent and said diluted solution.

6. The blood analyzer according to claim 1, wherein
said sample preparation portion is configured to prepare said second measurement sample by mixing at least said blood sample and said hemolytic agent stored in a second reagent container different from a first reagent container storing said hemolytic agent employed in said first measurement sample.

7. The blood analyzer according to claim 6, wherein
said hemolytic agent stored in said second reagent container is diluted by at least 9 times and not more than 12 times.

8. The blood analyzer according to claim 1, wherein
said hemolytic agent includes two types of cationic surfactants.

9. The blood analyzer according to claim 1, wherein
Said staining agent includes a fluorescent dye shown in the following formula and a nonionic surfactant

[Chemical Formula 1]

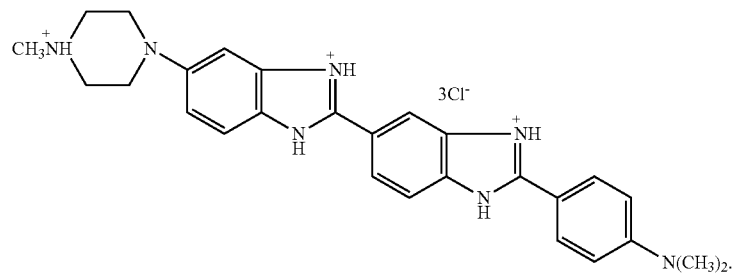

10. The blood analyzer according to claim 1, wherein
the two types of first scattered light information are forward scattered light information and side scattered light information, and
the second scattered light information is forward scattered light information.

11. The blood analyzer according to claim 8, wherein
each of the two types of cationic surfactants has 12 to 18 carbons and concentration of cationic surfactants in the first measurement sample is 0.62mM to 2.15 mM.

12. A blood analyzer comprising:
a sample preparation portion configured to prepare a first measurement sample and a second measurement sample;
a light information generation portion configured to generate first fluorescent information and at least two types of first scattered light information from said first measurement sample and to generate second fluorescent information and second scattered light information from said second measurement sample; and
a control portion configured to
instruct the sample preparation portion to prepare the first measurement sample by mixing a first aliquot of a blood sample and first aliquot of a hemolytic agent, and to prepare the second measurement sample by mixing a second aliquot of said blood sample, a second aliquot of said hemolytic agent, and a staining agent,
perform a first classification of white blood cells in said first measurement sample into at least four groups comprising monocytes, neutrophils, eosinophils and others on the basis of said first fluorescent information and said two types of first scattered light information generated by said light information generation portion, and
classify blood cells in said second measurement sample into at least malaria-infected red blood cells and others on the basis of said second fluorescent information and said second scattered light information generated by said light information generation portion, wherein
a dilution magnification of said hemolytic agent in said second measurement sample is smaller than a dilution magnification of said hemolytic agent in said first measurement sample.

\* \* \* \* \*